(12) United States Patent
Bakker et al.

(10) Patent No.: US 7,491,729 B2
(45) Date of Patent: Feb. 17, 2009

(54) 3-SUBSTITUTED 3,4-DIHYDRO-THIENO[2,3-D]PYRIMIDIN-4-ONE DERIVATIVES, PRODUCTION AND USE THEREOF

(75) Inventors: Margaretha Bakker, Seeheim-Jugenheim (DE); Wilfried Hornberger, Neustadt (DE); Andreas Kling, Mannheim (DE); Udo Lange, Mannheim (DE); Helmut Mack, Ludwigshafen (DE); Achim Moeller, Grundstadt (DE); Reinhold Mueller, Schifferstadt (DE); Kurt Schellhaas, Ludwigshafen (DE); Martin Schmidt, Bensheim (DE); Gerd Steiner, Kircheim (DE); Karsten Wicke, Altrip (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 4 days.

(21) Appl. No.: 10/539,708

(22) PCT Filed: Dec. 17, 2003

(86) PCT No.: PCT/EP03/14423

§ 371 (c)(1),
(2), (4) Date: Dec. 30, 2005

(87) PCT Pub. No.: WO2004/055024

PCT Pub. Date: Jul. 1, 2004

(65) Prior Publication Data

US 2006/0142317 A1   Jun. 29, 2006

(30) Foreign Application Priority Data

Dec. 18, 2002 (DE) ................................ 102 59 382

(51) Int. Cl.
*A01N 43/54* (2006.01)
*A61K 31/505* (2006.01)
*C07D 239/00* (2006.01)
*C07D 471/00* (2006.01)
*C07D 487/00* (2006.01)
*C07D 491/00* (2006.01)

(52) U.S. Cl. ..................................... 514/267; 544/250
(58) Field of Classification Search ............... 514/267; 544/250
See application file for complete search history.

(56) References Cited

U.S. PATENT DOCUMENTS

| | | | |
|---|---|---|---|
| 5,932,730 A | 8/1999 | Riechers et al. | |
| 6,159,962 A | 12/2000 | Steiner et al. | |
| 6,159,981 A * | 12/2000 | Steiner et al. | 514/252.11 |
| 6,222,034 B1 | 4/2001 | Steiner et al. | |
| 6,355,647 B1 | 3/2002 | Steiner et al. | |
| 6,387,912 B1 | 5/2002 | Steiner et al. | |
| 6,750,221 B1 * | 6/2004 | Garcia-Ladona et al. | 514/267 |
| 7,109,205 B2 | 9/2006 | Riechers et al. | |
| 7,119,097 B2 | 10/2006 | Riechers et al. | |
| 2004/0048815 A1 | 3/2004 | Herr | |
| 2004/0077638 A1 | 4/2004 | Geneste | |
| 2004/0202656 A1 | 10/2004 | Garcia-Ladona et al. | |
| 2006/0142317 A1 | 6/2006 | Bakker et al. | |
| 2006/0159678 A1 | 7/2006 | Geneste | |
| 2006/0235004 A1 | 10/2006 | Geneste | |
| 2007/0098721 A1 | 5/2007 | Hillen | |
| 2007/0203338 A1 | 8/2007 | Riechers | |
| 2007/0299074 A1 | 12/2007 | Netz | |
| 2008/0161322 A1 | 7/2008 | Geneste | |

FOREIGN PATENT DOCUMENTS

| | | |
|---|---|---|
| EP | 0 169 132 A | 8/1992 |
| WO | WO 95/31988 | 11/1995 |
| WO | WO01/24827 | 4/2001 |
| WO | WO2008/064292 | 5/2008 |

OTHER PUBLICATIONS

Cryan, J., et al., 5-HT1A and Beyond: The Role of Serotonin and its Receptors in Depression and the Antidepressant Response, Hum. Psychopharmacol. Clin. Exp. 15, 113-135 (2000).*
S. J. Starkey et al. "5-HT$_{iD}$ as well as 5-HT$_{1A}$ Autoreceptors Modulate 5-HR Release in the Guinea-pig Dorsal Raphe Nucleus" Neuropharmacology 33,(3/4) 1994 pp. 393-402.

* cited by examiner

*Primary Examiner*—James O. Wilson
*Assistant Examiner*—Erich A Leeser
(74) *Attorney, Agent, or Firm*—Dykema Gossett PLLC

(57) ABSTRACT

3-Substituted 3,4-dihydrothieno[2,3-d]pyrimidin-4-one derivatives, production and use thereof. The invention relates to 3,4-dihydrothieno[2,3-d]pyrimidin-4-one derivatives which are substituted in position 3 by 5-membered heteroaryl which may be fused to an aryl or heteroaryl radical, where the heteroaryl and, if appropriate, the fused aryl or heteroaryl radical may have 1, 2 or 3 substituents selected independently of one another from $C_{1-5}$-alkyl, $C_{1-5}$-alkoxy, $C_{1-5}$-alkylthio, halogen, CN, halo-$C_{1-5}$-alkyl, halo-$C_{1-5}$-alkoxy, hydroxy, —$NH_2$, —$N(R6)_2$, —NH(R6), aryl, aryloxy, aralkyl, aralkyloxy and heteroaryl, where the substituents aryl, aryloxy, aralkyl, aralkyloxy and heteroaryl may have 1, 2 or 3 substituents selected independently of one another from $C_{1-5}$-alkyl, $C_{1-5}$-alkoxy, $C_{1-5}$-alkylthio, halogen, CN, halo-$C_{1-5}$-alkyl, halo-$C_{1-5}$-alkoxy, hydroxy, —$NH_2$, —$N(R6)_2$ and —NH(R6). The preparation and use of these derivatives, especially for therapeutic purposes, e.g. for the treatment of depressions, are likewise described.

18 Claims, No Drawings

3-SUBSTITUTED 3,4-DIHYDRO-THIENO[2,3-D]PYRIMIDIN-4-ONE DERIVATIVES, PRODUCTION AND USE THEREOF

CROSS-REFERENCE TO RELATED APPLICATION

This application is a Section 371 National State Application of Application No. PCT/EP 2003/014423 filed on Dec. 17, 2003.

The invention relates to 3-substituted 3,4-dihydrothieno[2,3-d]pyrimidin-4-one derivatives, to their preparation and to their use in particular for therapeutic purposes, e.g. for the treatment of depressions.

CNS disorders currently affect large parts of the population. In particular, about 20% of all women and 12% of all men are affected during their lives by psychiatric disorders such as mental disorders, e.g. depressions.

At present, a large number of strategies are suggested for the treatment of psychiatric disorders, and some are also in use. For example, selective dopamine D4/5-HT$_2$ receptor antagonists such as risperidone (cf. also EP 0 196 132) and belaperidone,

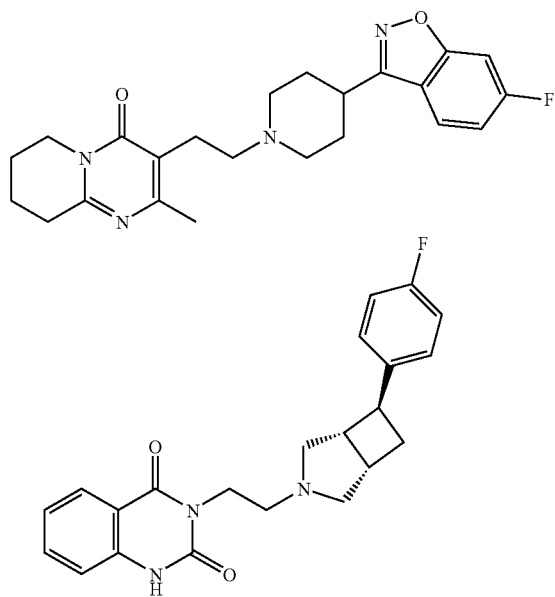

are proposed for the treatment of psychoses.

Another approach is to attempt to bring about the increase, which is regarded as the mechanism of the antidepressant effect, in the serotonin concentration in the synaptic cleft by on the one hand blocking the active reuptake of serotonin and/or presynaptic serotonin autoreceptors medically.

For example, classical antidepressants and also the newer selective serotonin reuptake inhibitors (SSRIs) such as, for example, paroxetine or fluoxetine develop their antidepressant effect inter alia by inhibiting the active reuptake of the transmitter into the presynaptic nerve endings. Unfortunately, in these cases the antidepressant effect has its onset only after treatment for at least 3 weeks. In addition, about 30% of patients are therapy-resistant.

Blockage of presynaptic serotonin autoreceptors is intended to abolish the negative feedback on serotonin release and thus increase the current transmitter concentration.

According to current knowledge, the presynaptic serotonin autoreceptor is of the 5-HT$_{1B/D}$ subtype. It may be remarked that the two genes encoding the human 5-HT$_{1B/D}$ subtype were initially referred to as 5-HT$_{1D\alpha}$ and 5-HT$_{1D\beta}$ and subsequently received the names 5-HT$_{1B}$ and 5-HT$_{1D}$. Selective blockade by 5-HT$_{1B/D}$ antagonists ought accordingly to increase the serotonin release in the brain. However, the serotonin release in the cortex after systemic administration of the selective 5-HT$_{1B}$ antagonist GR 127 935 is surprisingly reduced. One explanation might be stimulation of somatodendritic 5-HT$_{1A}$ receptors in the raphe region by the released serotonin, thus inhibiting the firing rate of serotonergic neurons and thus serotonin release.

A further strategy therefore attempts to bypass the autoinhibitory effects in serotonergic areas of origin by blocking both the presynaptic 5-HT$_{1B/D}$ receptors and the 5-HT$_{1A}$ receptor in order to increase terminal serotonin release and enhance neuronal firing, respectively (Starkey and Skingle, Neuropharmacology (1994) 33 (3-4) 393; cf. also WO 95/31988).

Following this strategy, certain 3-substituted 3,4-dihydrothieno[2,3-d]pyrimidine derivatives (WO 98/11110; WO 98/56792; WO 98/56793; WO 99/07711) having high affinity for the serotonin 5-HT$_{1B/D}$ and 5-HT$_{1A}$ receptors are proposed as active ingredients, for example for the treatment of depressions. In addition, neurodegenerative and neuropsychiatric disorders are indicated in WO 00/41696, and cerebral ischemia in WO 00/41695, as further therapeutic uses of these derivatives.

It has now been found, surprisingly, that further 3-substituted 3,4-dihydrothieno[2,3-d]pyrimidine derivatives have particularly valuable pharmacological properties and therefore appear to be particularly suitable for therapy.

The present invention therefore relates to compound of the formula (I)

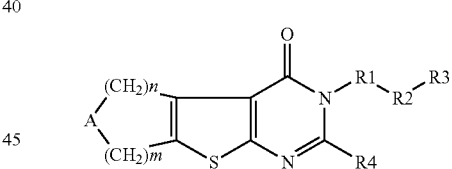

in which

A is O, S, SO, NR5 or CH$_2$;

R5 is H, C$_{1-5}$-alkyl, aryl, aralkyl, acyl or alkoxycarbonyl;

R4 is H or methyl;

n is 1 or 2;

m is 1 or 2;

R1 is C$_{1-8}$-alkylene;

R2 is a group of the formula

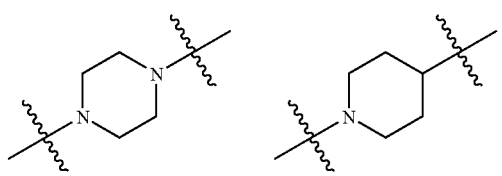

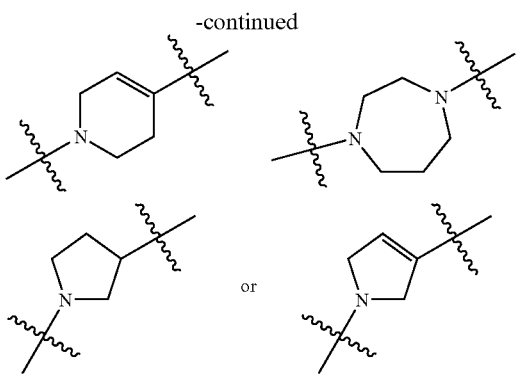

R3 is 5-membered heteroaryl which may be fused to an aryl or heteroaryl radical, where the heteroaryl and, optionally, the fused aryl or heteroaryl radical may have 1, 2 or 3 substituents selected independently of one another from $C_{1-5}$-alkyl, $C_{1-5}$-alkoxy, $C_{1-5}$-alkylthio, halogen, CN, halo-$C_{1-5}$-alkyl, halo-$C_{1-5}$-alkoxy, hydroxy, —$NH_2$, —$N(R6)_2$, —NH(R6), aryl, aryloxy, aralkyl, aralkyloxy and heteroaryl, where the substituents aryl, aryloxy, aralkyl, aralkyloxy and heteroaryl may have 1, 2 or 3 substituents selected independently of one another from $C_{1-5}$-alkyl, $C_{1-5}$-alkoxy, $C_{1-5}$-alkylthio, halogen, CN, halo-$C_{1-5}$-alkyl, halo-$C_{1-5}$-alkoxy, hydroxy, —$NH_2$, —$N(R6)_2$ and —NH(R6); and the radicals R6 are independently of one another $C_{1-5}$-alkyl, and physiologically tolerated salts thereof.

Preferred embodiments of this subject matter are described in the appended claims.

Physiologically tolerated salts include in the present case mainly acid addition salts, among which are numbered in particular salts of the compounds of the invention with inorganic acids such as hydrochloric acid, sulfuric acid, nitric acid or phosphoric acid, or organic acids, in particular carboxylic acids, e.g. acetic acid, tartaric acid, lactic acid, citric acid, malic acid, mandelic acid, ascorbic acid, maleic acid, fumaric acid, gluconic acid or sulfonic acids, e.g. methanesulfonic acid, benzenesuffonic acid and toluenesulfonic acid, and the like.

Where the compounds of the invention have centers of asymmetry, racemates and optical isomers as mixtures or in pure form (enantiomers, diastereomers) are included. Mixtures of enantiomers can be used for therapeutic purposes. Diastereomers are preferably, because of differences in physicochemical properties, used as substantially pure diastereomers.

The term "alkyl, alkoxy etc." comprises straight-chain or branched alkyl groups such as —$CH_3$, —$C_2H_5$, n-propyl, —$CH(CH_3)_2$, n-butyl, —$CH(CH_3)$—$C_2H_5$, isobutyl, —$C(CH_3)_3$, n-pentyl or n-hexyl, in particular $CH_3$, $C_2H_5$ or $CH(CH_3)_2$, preferably with—unless otherwise indicated—1 to 8, in particular 1 to 6 and particularly preferably 1 to 5, carbon atoms; "alkyl, alkoxy etc." as substituent of the radical R3 preferably comprises 1 to 3 carbon atoms. Alkylthio is preferably —$SCH_3$.

The term "haloalkyl" means alkyl partially or completely substituted by fluorine, chlorine, bromine and/or iodine, that is for example $CH_2F$, $CHF_2$, $CF_3$, $CH_2Cl$, 2-fluoroethyl, 2-chloroethyl or 2,2,2-trifluoroethyl; haloalkyl as substituent of the radical R3 is preferably $CHF_2$ and especially $CF_3$.

The term "haloalkoxy" means alkoxy partially or completely substituted by fluorine, chlorine, bromine and/or iodine, that is for example the haloalkoxy radicals corresponding to the haloalkyl radicals listed above; haloalkoxy as substituent of the radical R3 is preferably $OCHF_2$ and especially $OCF_3$.

Acyl means —COR in which R may be alkyl, aryl or aralkyl. Acyl is accordingly in particular $C_{1-5}$-alkyl-CO—, aryl-CO—, arylmethyl-CO— and arylethyl-CO—, e.g. acetoxy and benzoyl.

Alkoxycarbonyl means —COOalkyl preferably having 1 to 5 carbon atoms in the alkyl moiety, that is $C_{1-5}$-alkyl-O—CO—, such as —CO—$OCH_3$, —CO—$OC_2H_5$, —CO—$OCH_2$—$C_2H_5$, —CO—$OCH(CH_3)_2$, n-butoxycarbonyl, —CO—$OCH(CH_3)$—$C_2H_5$, —CO—$OCH_2$—$CH(CH_3)_2$, —CO—$OC(CH_3)_3$, in particular —CO—$OCH_3$, —CO—$OC_2H_5$, —CO—$OCH(CH_3)_2$ or —CO—$OCH_2$—$CH(CH_3)_2$.

Aryl means in particular an aromatic system having a 5- or 6-membered ring structure which may be fused to an aryl radical and is preferably naphthyl and in particular phenyl.

Heteroaryl means in particular an aromatic system which comprises 1, 2, 3 or 4 heteroatoms selected independently from O, N and S and has a 5- or 6-membered ring structure which comprises the heteroatoms and carbon atoms and may be fused to an aryl or heteroaryl radical. Heteroaryl having a 6-membered ring structure includes nitrogen-containing radicals such as pyridyl, pyrimidyl, pyridazinyl, pyrazinyl, quinolinyl and isoquinolinyl.

The term "5-membered heteroaryl" means in particular an aromatic system which comprises 1, 2, 3 or 4 heteroatoms selected independently from O, N and S and has a 5-membered ring structure comprising the heteroatoms and carbon atoms. Included herein are nitrogen-containing radicals such as pyrrolyl, imidazolyl, pyrazolyl, 1,2,4-triazolyl, tetrazolyl; oxygen-containing radicals such as furanyl; sulfur-containing radicals such as thienyl; and radicals having at least two different heteroatoms, such as thiazolyl, isothiazolyl, 1,3,4-thiadiazolyl, 1,2,4-thiadiazolyl, 1,2,5-thiadiazolyl, isoxazolyl, oxazolyl.

5-Membered heteroaryl which is fused to an aryl or heteroaryl radical is in particular the heteroaryl which is explained above and is fused to 6-membered aryl or heteroaryl. Mention should be made in particular in this connection of 5-membered heteroaryl which is fused to a phenyl radical, i.e. benzo-fused heteroaryl such as indolyl, benzofuranyl, benzothienyl, indazolyl, benzimidazolyl, benztriazolyl, benzoxazolyl, benzisoxazolyl, benzthiazolyl, benzisothiazolyl, and 5-membered heteroaryl which is fused to a pyridyl radical, such as pyrrolopyridinyl and pyridisoxazolyl.

Aryloxy means aryl linked via oxygen.

Aralkyl means aryl linked via alkylene, where alkylene in this case preferably has 1 to 3 carbon atoms and is preferably benzyl.

Aralkyloxy means aralkyl linked via oxygen, in particular aryl-$CH_2$—O—, e.g. benzyloxy.

The term "halogen" comprises a fluorine, chlorine, bromine or iodine atom and in particular a fluorine, chlorine or bromine atom. Preference is given ordinarily to fluorine and chlorine atoms, if appropriate also bromine atoms.

If aromatic radicals are substituted according to the invention, the substituents are preferably to be selected from $C_{1-5}$-alkyl, $C_{1-5}$-alkoxy, $C_{1-5}$-alkylthio, halogen, CN, halo-$C_{1-5}$-alkyl, halo-$C_{1-5}$-alkoxy, hydroxy, —$NH_2$, —$N(R_6)_2$, —NH($R_6$), aryl, aryloxy and aralkyloxy.

The term "alkylene" comprises straight-chain or branched divalent alkylene groups, preferably having—unless indicated otherwise—1 to 8, in particular 1 to 6 and particularly preferably 1 to 4, carbon atoms. Mention should be made in particular of alkylene radicals such as methylene, eth-1,2-ylene, prop-1,2-ylene, prop-1,3-ylene, but-1,2-ylene, but-1,3-ylene, but-2,3-ylene, but-1,4-ylene, 2-methylprop-1,3-ylene, pent-1,2-ylene, pent-1,3-ylene, pent-1,4-ylene, pent-1,5-ylene, pent-2,3-ylene, pent-2,4-ylene, 1-methylbut-1,4-ylene, 2-methylbut-1,4-ylene, 2-methylbut-1,3-ylene, 2-ethylprop-1,3-ylene, hex-3,4-ylene, 3-methylpent-2,4-ylene, hept-3,5-ylene, 2-ethylpent-1,3-ylene, 3-ethylhept-3,5-ylene, etc.

The compounds of the invention belong to the class of 3-substituted 3,4-dihydrothieno[2,3-d]pyrimidin-4-one derivatives. These compounds have in the 5,6 position a cycloaliphatic or heterocyclic radical which is formed from the alkylene radicals $(CH_2)_n$ and $(CH_2)_m$ respectively located in the 5 and 6 positions, and the divalent radical A.

The compounds of the invention preferably have a heterocycle in the 5,6 position of the thieno[2,3-d]pyrimidin-4-one structure. The radical A is advantageously O, S and in particular NR5.

If A is NR5, then R5 is preferably hydrogen or $C_{1-5}$-alkyl, advantageously hydrogen or methyl.

The cyclic or heterocyclic aliphatic radical linked in the 5,6 position of the thieno[2,3-d]pyrimidin-4-one structure forms preferably a 5- and in particular 6-membered ring. The total of n+m is therefore preferably 2 and in particular 3.

In one embodiment, the present invention relates to 3-substituted 5,6,7,8-tetrahydro-pyridothieno[2,3-d]pyrimidin-4(3H)-one derivatives, namely compounds of the formula (I) in which A is NR5 and the total of n+m is 3. These include in particular 3-substituted 5,6,7,8-tetrahydropyrido[4',3':4,5]thieno[2,3-d]pyrimidin-4(3H)-one derivatives (n=2; m=1) and 3-substituted 5,6,7,8-tetrahydropyrido[3',4':4,5]thieno[2,3-d]pyrimidin-4-(3H)-one derivatives (n=1; m=2), with preference for the former.

In a further embodiment, the present invention relates to 3-substituted 3,5,6,8-tetrahydro-4H-pyrano[4',3':4,5]thieno[2,3-d]pyrimidin-4-one, 3-substituted 3,5,6,8-tetrahydro-4H-thiopyrano[4',3':4,5]thieno[2,3-d]pyrimidin-4-one and 3-substituted 5,6,7,8-tetrahydro[1]benzothieno[2,3-d]pyrimidin-4(3H)-one derivatives, namely compounds of the formula (I) in which A is respectively oxygen, sulfur and methylene, and n is 2 and m is 1.

In a further embodiment, the present invention relates to 3-substituted 3,5,6,7-tetrahydro-4H-pyrrolo[3',4':4,5]thieno[2,3-d]pyrimidin-4-one, 3-substituted 5,7-dihydro-furo[3',4':4,5]thieno[2,3-d]pyrimidin-4(3H)-one, 3-substituted 5,7-dihydro-thieno[3',4':4,5]thieno[2,3-d]pyrimidin-4(3H)-one and 3-substituted 3,5,6,7-tetrahydro-4H-cyclopenta[4,5]thieno[2,3-d]pyrimidin-4-one derivatives, namely compounds of the formula (I) in which A is respectively NR5, oxygen, sulfur and methylene, and n is 1 and m is 1, with preference for compounds with A=NR5 and methylene.

The compounds of the invention are preferably unsubstituted in position 2, i.e. R4 is hydrogen.

The substituent in position 3 of the thieno[2,3-d]pyrimidin-4-one structure is composed of a divalent group R1 which creates a certain distance from the structure, of a 5-, 6- or 7-membered aliphatic, monocyclic heterocycle R2 comprising 1 or 2 nitrogen atoms, and of a terminal heteroaromatic group R3.

Accordingly, R1 is alkylene which may be straight-chain or branched and whose main chain preferably has a length of 2 or 3 and in particular of 2 carbon atoms. If the alkylene is branched, the main chain preferably has a substituent selected from among methyl and ethyl. Preferred alkylene radicals R1 therefore include in particular the straight-chain radicals eth-1,2-ylene and prop-1,3-ylene and the branched radicals prop-1,2-ylene, 2-methylprop-1,3-ylene, but-1,2-ylene and but-1,3-ylene.

The nitrogen-containing heterocycle R2 may be saturated or unsaturated. Unsaturated heterocycles have 1 double bond. The heterocycle is normally connected to the radical R1 via a nitrogen atom and to the radical R3 via a nitrogen or a carbon atom. If the heterocycle has a double bond, this is preferably located on the carbon atom linked to R3. The radicals R1 and R3 are linked preferably via positions 1 and 3 in 5-membered heterocycles, preferably via positions 1 and 4 in 6-membered heterocycles and preferably via positions 1 and 4 in 7-membered heterocycles.

In a particular embodiment, the present invention relates to compounds of the formula (I) in which R2 is a 6-membered heterocycle which has 1 or 2 nitrogen atoms and may have a double bond and is in particular a group of the formula

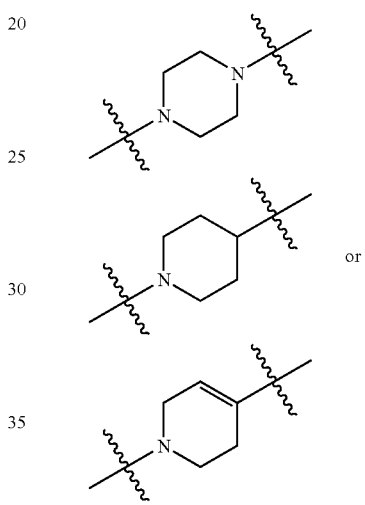

or namely piperazin-1,4-yl, piperidin-1,4-yl or 1,2,3,6-tetrahydropyridin-1,4-yl, where the 1 position is preferably linked to the radical R1 and the 4 position preferably to the radical R3.

It should be noted that advantageous embodiments are possible for the heterocyclic radical R2, depending on the nature of the heteroaromatic radical R3. R2 is preferably to be selected so that the group R2-R3 does not form an enamine.

The compounds of the invention comprise the radical R2 linked to a 5-membered heteroaromatic radical (heteroaryl). In addition, these 5-membered heteroaromatic rings may have further fused rings; in this case, the respective 5-membered aromatic ring and a further aromatic (aryl) or heteroaromatic (heteroaryl) ring share two adjacent ring atoms.

In a particular embodiment, the present invention relates to compounds of the formula (I), in which R3 is a group of the formula (VIII)

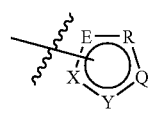

in which
E is N or C;
x is N, S, C or CR10;

Y is N, NR11, O, S or CR11;

Q is N or CR9;

R is N, NR8 or CR9;

R8, R9, R10, R11 are independently of one another hydrogen, $C_{1-5}$-alkyl, $C_{1-5}$-alkoxy, $C_{1-5}$-alkylthio, halogen, CN, halo-$C_{1-5}$-alkyl, halo-$C_{1-5}$-alkoxy, hydroxy, —$NH_2$, —$N(R6)_2$, —NH(R6), aryl, aryloxy, aralkyl, aralkyloxy and heteroaryl, where the substituents aryl, aryloxy, aralkyl, aralkyloxy or heteroaryl may in turn be substituted, or R8 and R9 together with the nitrogen or carbon atoms to which they are bonded form an optionally substituted 5- or 6-membered aryl or heteroaryl radical; and the radicals R6 have independently of one another the above meaning.

Particularly preferred compounds of the formula (I) disclosed above are those in which R3 is a group of the formula (VIIIa)

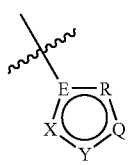

in which E, X, Y, Q, R, R8, R9, R10, R11 and R6 have the above meanings.

In a particular embodiment, the present invention relates to compounds of the formula (I) in which R3 is a group of the formula (VIIIa), and E is carbon, X is nitrogen and Y is oxygen. It is additionally advantageous for these 5-membered heteroaromatic radicals to be fused, in which case benzene and pyridine are particularly suitable for fusion.

In the embodiment described above, the present invention therefore relates to particularly advantageous compounds of the formula (I) in which R3 is a fused group of the formula (IX)

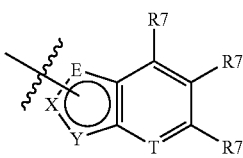

in which

E is N or C;

X is N, S, C or CH;

Y is N, NR11, O, S or CR11;

T is CR7 or N;

R11 has the above meanings and is preferably H or $C_{1-5}$-alkyl; and the radicals R7 are independently of one another H, $C_{1-5}$-alkyl, $C_{1-5}$-alkoxy, $C_{1-5}$-alkylthio, halogen, CN, halo-$C_{1-5}$-alkyl, halo-$C_{1-5}$-alkoxy, hydroxy, —$NH_2$, —$N(R6)_2$ or —NH(R6).

Particularly preferred advantageous compounds of the formula (I) of those disclosed above are particularly those in which R3 is a group of the formula (IXa)

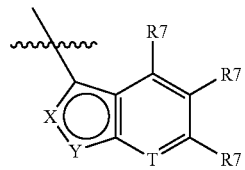

in which X, Y, T, the radicals R7, R11 and R7 have the above meanings.

The invention in this embodiment therefore relates in particular to compounds of the formula (I) in which R3 is optionally substituted 1H-indol-3-yl, 1H-pyrrolo[2,3-b]pyridin-3-yl 1-benzofuran-3-yl, 1-benzothien-3-yl, 1H-indazol-3-yl, 1H-benzimidazol-1-yl, 1H-benzimidazol-2-yl, 1H-benzotriazol-1-yl, 1,3-benzoxazol-2-yl, 1,2-benzisoxazol-3-yl, 1,3-benzothiazol-2-yl and 1,2-benzisothiazol-3-yl, with particular preference for 1,2-benzisoxazol-3-yl.

Of the non-fused 5-membered heteroaromatic groups, mention should be made in particular of 1H-pyrazol-3-yl, 1H-tetrazol-5-yl, 1,3-thiazol-2-yl and 1,2,4-thiadiazol-5-yl These may have 1, 2 or 3 substituents selected independently of one another from $C_{1-5}$-alkyl, $C_{1-5}$-alkoxy, $C_{1-5}$-alkylthio, halogen, CN, halo-$C_{1-5}$-alkyl, halo-$C_{1-5}$-alkoxy, hydroxy, —$NH_2$, —$N(R6)_2$ or —NH(R6), aryl, aryloxy, aralkyl, aralkyloxy and heteroaryl, where the substituents aryl, aryloxy, aralkyl, aralkyloxy and heteroaryl in turn may have 1, 2 or 3 substituents selected independently of one another from $C_{1-5}$-alkyl, $C_{1-5}$-alkoxy, halogen, CN, $SCH_3$, trifluoromethyl, hydroxy, —$N(C_{1-5}$-alkyl$)_2$, —NH($C_{1-5}$-alkyl) or —$NH_2$.

In a further aspect of the invention, the heteroaromatic groups described above in connection with the radical R3 are monosubstituted. Accordingly, R3 is preferably a radical of the formula

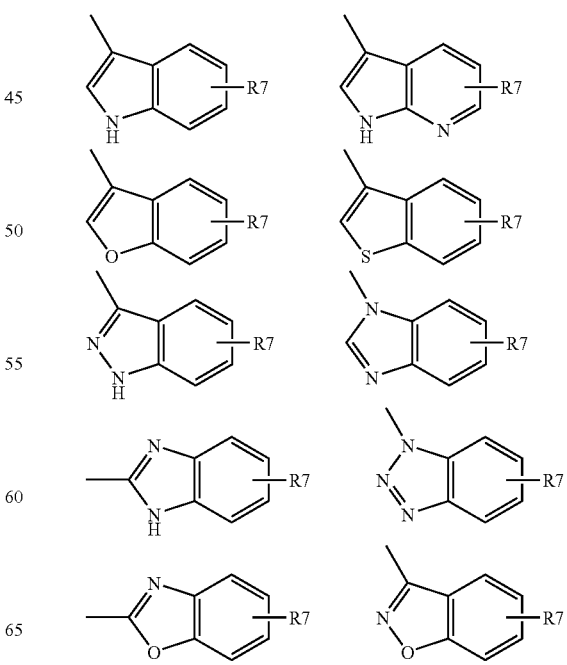

-continued

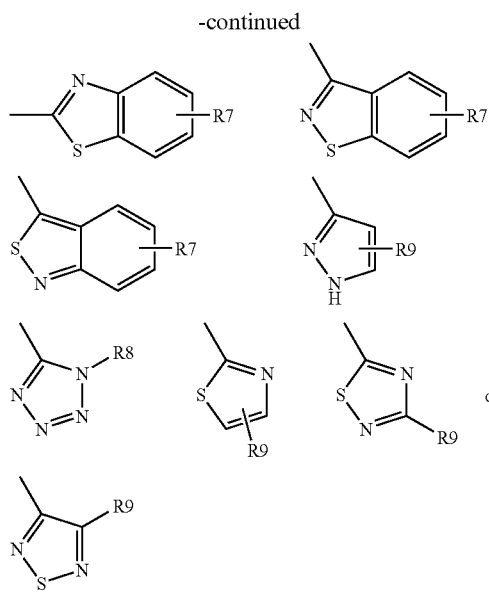

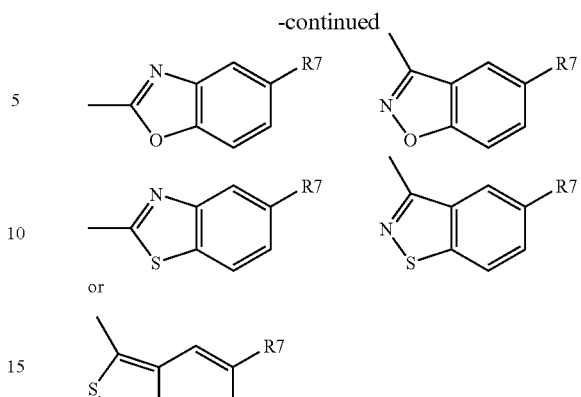

or

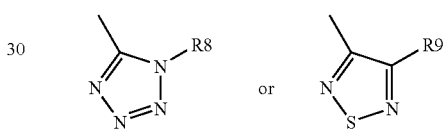

in which

R7 is H, $C_{1-5}$-alkyl, $C_{1-5}$-alkoxy, $C_{1-5}$-alkylthio, halogen, CN, halo-$C_{1-5}$-alkyl, halo-$C_{1-5}$-alkoxy, hydroxy, —NH$_2$, —N(R6)$_2$ or —NH(R6);

R8 is H, $C_{1-5}$-alkyl, aryl, aralkyl and heteroaryl, where aryl, aralkyl and heteroaryl may in turn be substituted in the manner described above; and R9 is H, $C_{1-5}$-alkyl, $C_{1-5}$-alkoxy, $C_{1-5}$-alkylthio, halogen, CN, halo-$C_{1-5}$-alkyl, halo-$C_{1-5}$-alkoxy, hydroxy, —NH$_2$, —N(R6)$_2$, —NH(R6), aryl, aryloxy, aralkyl, aralkyloxy or heteroaryl, where aryl, aryloxy, aralkyl, aralkyloxy and heteroaryl may in turn be substituted in the manner described above.

In a particularly preferred embodiment, the present invention relates to compounds of the formula (I) in which R3 is a group of the formula where R7 is as defined above. Of these, the benzisoxazol-3-yl radical and the 1H-pyrrolo[2,3-b]pyridin-3-yl radical are very particularly preferred.

In a further particularly preferred embodiment, the present invention relates to compounds of the formula (I) in which R3 is a group of the formula where R8 and R9 are as defined above.

In the compounds of the invention in the embodiments explained above, R7 as substituent of the fused heteroaromatic radicals is in particular $C_{1-5}$-alkyl, preferably methyl, halogen, preferably chlorine, or halo-$C_{1-5}$-alkyl, preferably trifluoromethyl; R8 as substituent of non-fused heteroaromatic radicals is in particular $C_{1-5}$-alkyl, preferably methyl, ethyl or isopropyl, or aryl, preferably phenyl, which may be substituted; and R9 as substituent of non-fused heteroaromatic radicals is in particular $C_{1-5}$-alkoxy, preferably methoxy, ethoxy or isopropoxy, aryl, preferably phenyl, which may be substituted, e.g. by chlorine, or heteroaryl, e.g. 2-thienyl.

The compounds of the invention can be prepared in a manner known per se. Reference is made in particular to the processes disclosed in WO 98/11110; WO 98/56792; WO 98/56793 and WO 00/41695 for preparing the thieno[2,3-d]pyrimidin-4-one derivatives described therein. Accordingly it is possible to choose various procedures which differ basically in that the substituent in position 3 of the thieno[2,3-d]pyrimidin-4-one structure is introduced as a unit already comprising the radicals R1, R2 and R3, or firstly a unit comprising only the radical R1 or the radicals R1 and R2 is introduced and subsequently reaction is carried out in a suitable manner with further units comprising the radicals R2 and R3 or R3.

The present invention therefore also relates to a process for preparing compounds of the invention of the formula (I) by reacting a compound of the formula (II)

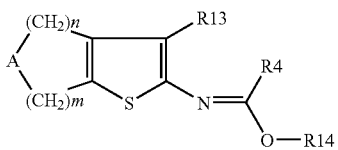

in which A, n, m and R4 have one of the meanings indicated above; R13 is CN or $C_{1-3}$-alkyl-O—CO—, and R14 is $C_{1-3}$-alkyl,
with a primary amine of the formula (III)

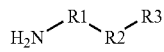

in which R1, R2 and R3 have one of the meanings indicated above.

This reaction can be carried out either without solvent or expediently in an inert organic solvent, for example a short-chain alcohol such as methanol or ethanol, or a cyclic saturated ether such as tetrahydrofuran or dioxane.

A reaction temperature is chosen usually in the range from 20 to 190° C., in particular in a range from 60 to 90° C. The reaction is usually complete within 1 to 10 hours.

The present invention further relates to an alternative process for preparing compounds of the invention of the formula (I) initially by reacting a compound of the formula (II)

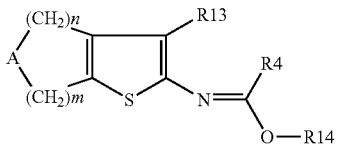

in which A, n, m and R4 have one of the meanings indicated in claim 1; R13 is CN or $C_{1-3}$-alkyl-O—CO—, and R14 is $C_{1-3}$-alkyl,
with a primary amine of the formula (IV)

in which R1 has one of the meanings indicated above.

This reaction is carried out similar to the above reaction in an inert solvent, preferably alcohols such as ethanol, at a reaction temperature in the range from 60 to 120° C.

Subsequently, the terminal hydroxyl function of the cyclic product is halogenated. This can take place by reacting the resulting compound of the formula (V)

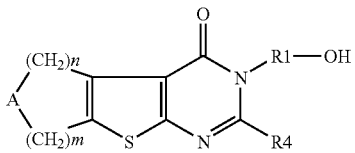

in which A, n, m, R4 and R1 have one of the meanings indicated above,
with a halogenating agent such as thionyl chloride.

Further suitable halogenating agents such as hydrobromic acid are known to the skilled worker. The reaction is carried out either without solvent or expediently in an organic solvent such as a halogenated hydrocarbon, at a reaction temperature of up to 100° C.

Finally, the halogenated product is converted into the desired compound of the formula (I). This takes place by reacting the resulting compound of the formula (VI)

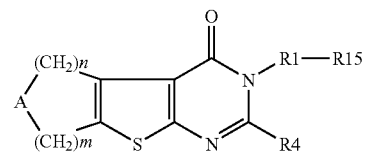

in which A, n, m, R4 and R1 have one of the meanings indicated above, and R15 is halogen,
with a secondary amine of the formula (VII)

in which R2 and R3 have one of the meanings indicated above. This variant is conditional on the radical R2 having a secondary nitrogen via which the radical R2 is to be linked to the radical R1. This reaction takes place advantageously in an inert organic solvent, preferably toluene, xylene, dimethylformamide or N-methylpyrrolidone, in the presence of a base such as potassium carbonate, potassium hydroxide or diisopropylethylamine at a reaction temperature in the range from RT to 150° C.

The compounds of the invention of the formula (I) can, just like the intermediates of the formulae (II), (V) and (VI) which are produced if appropriate, be isolated and, if necessary, purified in a conventional manner, for example by recrystallization from usual organic solvents, preferably a short-chain alcohol such as ethanol, or with the aid of chromatographic techniques.

Depending on the starting materials, the compounds of the invention of the formula (I) are produced in free form or already as acid addition salts. Both the compounds in free form and salts of these compounds resulting in the process can be converted in a manner known per se into the desired acid addition salts and into the free form, respectively.

The compounds of the invention have useful pharmacological properties. In particular, they have high affinity for $5\text{-HT}_{1B/D}$ and $5\text{-HT}_{1A}$ receptors.

A pharmacologically particularly valuable class of compounds of the invention comprises those which naturally antagonize effects caused by serotonin on $5\text{-HT}_{1B/D}$ and $5\text{-HT}_{1A}$ receptors.

The compounds of the invention can be used, because of their pharmacological properties, as active ingredients for therapeutic purposes.

The present invention therefore also relates further to compositions, in particular pharmaceutical compositions which comprise at least one compound of the invention and, if necessary, physiologically acceptable excipients.

Physiologically acceptable excipients are those which are known to be usable in the area of pharmacy and adjacent sectors, in particular those listed in relevant pharmacopeias (e.g. DAB, Ph. Eur., BP, NF, USP), and also other excipients whose properties do not stand in the way of physiological use.

Suitable excipients may be: wetting agents; emulsifying and suspending agents; preserving agents; antioxidants; anti-irritants; chelating agents; tablet-coating agents; emulsion stabilizers; film formers; gel formers; odor-masking agents; masking flavors; resins; hydrocolloids; solvents; solubilizers; neutralizers; permeation promoters; pigments; quaternary ammonium compounds; refatting and superfatting agents; ointment, cream or oil bases; silicone derivatives; spreading aids; stabilizers; sterilizers; suppositories bases; tablet excipients such as binders, fillers, lubricants, disintegrants or coatings; propellants; desiccants; opacifiers; thickeners; waxes; plasticizers; white oils. An arrangement concerning this is based on specialist knowledge as described for example in Fiedler, H. P., Lexikon der Hifsstoffe für Pharmazie, Kosmetik und angrenzende Gebiete, 4$^{th}$ edition, Aulendorf: ECV-Editio-Cantor-Verlag, 1996.

Examples of suitable pharmaceutical compositions are solid drug forms such as oral powders, dusting powders, granules, tablets, especially film-coated tablets, pastilles, sachets, cachets, sugar-coated tablets, capsules such as hard and soft gelatin capsules, suppositories or vaginal drug forms, semisolid drug forms such as ointments, creams, hydrogels, pastes or patches, and liquid drug forms such as solutions, emulsions, especially oil-in-water emulsions, suspensions, for example lotions, preparations for injection and infusion, eye drops and ear drops. Implanted delivery devices can also be used to administer active ingredients of the invention. Liposomes or microspheres can also be used in addition.

The compositions may be administered for example in the customary manner.

In the production of compositions, the active ingredients are usually mixed or diluted with a suitable excipient. Excipients may be solid, semisolid or liquid materials which serve as vehicle, carrier or medium for the active ingredient. Admixture of further excipients takes place if necessary in a manner known per se. Shaping steps can be carried out, if appropriate in conjunction with mixing processes, e.g. a granulation, compression and the like.

The use according to the invention for therapeutic purposes relates in particular to the treatment of disorders of the central nervous system. By these are meant disorders affecting the brain in particular. The term "disorder" in the sense according to the invention refers to abnormalities which are usually regarded as pathological states and may reveal themselves in the form of particular signs, symptoms and/or dysfunctions. The treatment according to the invention may be directed at individual disorders, i.e. abnormalities or pathological states, but it is also possible for a plurality of abnormalities, which are causally connected together if appropriate, to be combined into patterns, i.e. syndromes, which can be treated according to the invention.

The disorders which can be treated according to the invention include in particular neurological and psychiatric disorders.

Neurological disorders include neurodegenerative disorders, especially neurodegenerative disorders connected with aging processes, demyelinating processes, ischemic events and/or other morphological changes. The morphological changes include in particular those associated with neuronal changes and, in particular, deficits, e.g. neurodegenerative disorders connected with infections, traumata, tumors, deposits and/or diffuse atrophic changes in the brain. Neurological disorders which can be treated according to the invention include impairments of mental functions, especially dementia, in particular cerebrovascular dementia and Alzheimer-type dementia, e.g. senile dementia and Alzheimer's disease, especially intellectual deficits such as attention deficit disorders, amnesic and cognitive disorders, e.g. learning and memory impairment (impaired cognitive function); multiple sclerosis; Parkinson's; epilepsy; delirium; disorders of attention and waking/sleeping behavior, especially behavioral disturbances and emotional disturbances starting in childhood and adolescence, such as hyperactivity in children; narcolepsy and sleep disorders, e.g. restless legs syndrome; developmental disorders.

Psychiatric disorders include psychoses, e.g. of the acute exogenous type or associated psychoses with an organic or exogenous cause, e.g. after trauma, especially brain lesions and diffuse brain damage, associated with metabolic disorders, infections and endocrinopathies; endogenous psychoses such as schizophrenia, and schizotypal and delusional disorders; affective disorders such as depressions, mania and manic-depressive states; and combined forms of the disorders described above; neurotic and somatoform disorders, and disorders associated with stress; dissociative disorders, e.g. deficits, clouding and splitting of consciousness, and personality disorders; anxiety states; disorders of the sex life, e.g. impotence in men; depressive states associated with other disorders, e.g. in connection with fibromyalgia and chronic fatigue syndrome; eating disorders, e.g. anorexia or bulimia; and other undefined psychiatric disorders.

A particularly preferred embodiment of the present invention is directed at the treatment of depressions.

It is possible by the treatment according to the invention to treat a large number of signs, symptoms and/or dysfunctions which are connected with the disorders and in particular the aforementioned states. These include for example symptoms of dementia, especially those affecting social relations, a decline in intellectual functions, e.g. confusion, especially temporal and spatial, disorders of memory and association, and of the capacity for abstract thought and judgment, an impaired relation to reality, lack of insight and ability to comply with the usual social norms and demands of life, changes in behavior, changes in individual urges such as hunger, sleep, thirst etc., and in mood, personality changes, especially emotional lability, hallucinations, ego disturbances, incoherence of thought, ambivalence, autism, depersonalization or hallucinations, delusional ideas, staccato speech, absence of syncynesis, small-step gait, bent posture of trunk and limbs, tremor, mask-like face, monotonous speech, depressions, apathy, deficient spontaneity and irresolution, reduced association ability, anxiety, nervous agitation, stammering, social phobia, panic disorders, expansive syndromes, states of agitation and confusion, dysphoria, dyskinetic syndromes and tic disorders, e.g. associated with Huntington's chorea, Gilles-de-la-Tourette syndrome, vertigo syndromes, e.g. peripheral postural, rotational and vestibular vertigo, melancholia, hysteria, hypochondria and the like.

The use according to the invention of the active ingredients of the invention comprises a method within the scope of the treatment. This entails the subject to be treated, preferably a mammal, in particular a human, and also an agricultural or domestic animal, being given an effective amount of at least one compound of the formula (I), usually formulated in accordance with pharmaceutical practice.

The invention also relates to the production of compositions for the treatment of a subject, preferably of a mammal, in particular of a human, agricultural or domestic animal.

The following examples illustrate the invention without restricting it.

It should be noted that the naming and depiction of formulae of salts with protonated nitrogen represent merely one of a plurality of possibilities, all of which are included, relating to the charge distribution. This also applies to tautomeric forms.

A Preparation of the Starting Materials of the Formula (II), (V) and (VI)

The 2-amino-3-carboethoxy(cyano)-4,5,6,7-tetrahydrothieno[2,3-c]pyridines with methyl, benzyl, acetyl, benzoyl group in position 6 or with unsubstituted 6 position, which are employed as starting materials of the formula (II), are disclosed in the literature (K. Gewald et al, Chem. Ber. 99, 94-100 (1966)). The preparation of these starting materials is also described in WO 98/11110; WO 98/56793.

A1) 2-Ethoxymethyleneamino-3-carboethoxy-6-methyl4,5,6,7-tetrahydrothieno[2,3-c]pyridine (Starting Material of the Formula (II))

40.0 g (167 mM) of 2-amino-3-carboethoxy-6-methyl-4,5,6,7-tetrahydrothieno[2,3-c]pyridine in 250 ml of triethyl orthoformate were mixed with 3.2 ml of acetic anhydride and refluxed under nitrogen for 3 h. The mixture was then concentrated completely in a rotary evaporator at 80° C. 48.0 g (97%) of crude product were isolated as a dark oil which is sufficiently pure for further reaction.

A2) 3-(2-Hydroxyethyl)-7-methyl-5,6,7,8-tetrahydropyrido[4',3':4,5]thieno[2,3-d]pyrimidin-4(3H)-one (Starting Materials of the Formula (V))

86.4 g (292 mM) of 2-ethoxymethyleneamino-3-carboethoxy-6-methyl-4,5,6,7-tetrahydrothieno[2,3-c]pyridine in 200 ml of ethanol were mixed with 17.6 ml (292 mM) of ethanolamine and refluxed for 2 h. The mixture was then concentrated in vacuo, and the residue was taken up in 30 ml of ethyl acetate with stirring. The solid which precipitated overnight was filtered off with suction and washed with a little ethyl acetate. After recrystallization from ethanol, 48.0 g (62%) of product with melting point 163-165° C. were isolated.

A3) 3-(2-Chloroethyl)-7-methyl-5,6,7,8-tetrahydropyrido[4',3':4,5]thieno[2,3-d]pyrimidin-4(3H)-one (Starting Material of the Formula (VI))

42.0 g (158 mM) of 3-(2-hydroxyethyl)-7-methyl-5,6,7,8-tetrahydropyrido[4',3':4,5]thieno[2,3-d]pyrimidin-4-one in 240 ml of 1,2-dichloroethane were heated to reflux and then 12.7 ml (175 mM) of thionyl chloride in 20 ml of 1,2-dichloroethane were added dropwise. After refluxing for 2 h, the reaction mixture was allowed to cool and was poured into ice/water. The mixture was partitioned between methylene chloride and water at pH=10, and the aqueous phase was extracted with methylene chloride. The combined organic phases were dried and then concentrated. The crude product (40 g) was recrystallized from 400 ml of isopropanol. 30.5 g (68%) of product with melting point 159-161° C. were isolated.

The following were prepared in analogy to A1) to A3):

A4) 3,4,5,6,7,8-Hexahydro-3-(1-hydroxy)prop-2-yl-7-methyl pyrido[4',3':4,5]thieno[2,3-d]pyrimidin-4-one (Starting Material of the Formula (V))

A5) 3,4,5,6,7,8-Hexahydro-3-(1-chloro)prop-2-yl-7-methyl-pyrido[4',3':4,5]thieno[2,3-d]pyrimidin-4-one (Starting Material of the Formula (VI))

A6) 3-(2-Hydroxyethyl)-3,5,6,8-tetrahydro-4H-pyrano[4',3':4,5]thieno[2,3-d]pyrimimidin-4(3H)-one (starting from tetrahydro-4H-pyran-4-one)

(Starting Material of the Formula (V))

A7) 3-(2-Chloroethyl)-3,5,6,8-tetrahydro-4H-pyrano[4',3':4,5]thieno[2,3-d]pyrimidin-4(3H)-one (Starting Material of the Formula (VI))

A8) 3-(2-Hydroxyethyl)-3,5,6,8-tetrahydro-4H-thiopyrano[4',3':4,5]thieno[2,3-d]pyrimidin-4(3H)-one (starting from tetrahydro-4H-thiopyran-4-one)

(Starting Material of the Formula (V))

A9) 3-(2-Chloroethyl)-3,5,6,8-tetrahydro-4H-thiopyrano[4',3':4,5]thieno[2,3-d]pyrimidin-4(3H)-one (Starting Material of the Formula (VI))

B) Preparation of the Starting Materials of the Formula (VII):

B1) 3-Piperazin-1-yl-5-methyl-1,2-benzisoxazole

3-Chloro-5-methyl-1,2-benzisoxazole

3-Hydroxy-5-methyl-1,2-benzisoxazole (15.0 g, 100.6 mmol; preparation: Australian Journal of Chemistry (1977), 30(8), 1847-50) were suspended in triethylamine (15.4 ml, 110.6 mmol), and phosphorus oxytrichloride (37.0 g, 22.5 ml, 241.4 mmol) was added dropwise with cooling to this mixture at room temperature. Since stirring of the reaction mixture became almost impossible after about half the amount of phosphorus oxytrichloride had been added dropwise, the temperature was raised to 50° C. After dropwise addition of the total amount of phosphorus oxytrichloride, the reaction mixture was heated at 130° C. for 5 h, after which the reaction was complete according to TLC. After cooling, the mixture was slowly added dropwise to water (200 ml) while cooling, the aqueous phase was extracted 3 times with MtB ether, the organic phases were washed with water, dried over magnesium sulfate and concentrated in vacuo. This resulted in 14.6 g of 3-chloro-5-methyl-1,2-benzisoxazole (yield: 87%) as viscous oil which solidified overnight. MS (MSD) m/z 168 [M+H$^+$].

3-Piperazin-1-yl-5-methyl-1,2-benzisoxazole

3-Chloro-5-methyl-1,2-benzisoxazole (2.17 g, 12.93 mmol) was stirred together with piperazine (10.0 g, 116.1 mmol) and DBU (diazabicycloundecene; 2.0 g 13.14 mmol) in a melt at 120° C. for 4 h, after which the reaction was complete according to TLC. After cooling, the mixture was added to water, and the aqueous phase was extracted 3 times with dichloromethane, and the organic phases were washed with water, dried over magnesium sulfate and concentrated in vacuo. This resulted in 2.24 g of 3-piperazin-1-yl-5-methyl-1,2-benzisoxazole (yield: 80%) being obtained as a slightly impure solid product which was purified by chromatography.
MS (MSD) m/z 218 [M+H$^+$].

B2) 3-Piperazin-1-yl-7-methyl-1,2-benzisoxazole

7-Methyl-1,2-benzisoxazole (5 g, 33.52 mmol) was converted into the corresponding 3-chloro compound (0.7 g of oil) in analogy to Boeshagen et al., Chem. Ber. 100, 10, 1967, 3326-3330, and subsequently converted in analogy to preparation of 3-piperazin-1-yl-1,2-benzisoxazole into the corresponding 3-piperazin-1-yl-7-methyl-1,2-benzisoxazole (0.18 g of yellowish oil, MS (ESI) m/z 218 [M+H$^+$]).

B3) 3-Piperazin-1-yl-5-methoxy-1,2-benzisoxazole

5-Methoxy-3-chloro-1,2-benzisoxazole (4.7 g, 25.6 mmol) prepared by the method of Boeshagen et al., Chem. Ber. 100, 10, 1967, 3326-3330, piperazine (19.8 g, 229.86 mmol) and 6 ml of DBU were heated at 120° C. for 2 h and then taken up in CH$_2$Cl$_2$, washed with water, and dried and evaporated. The residue obtained in this way (6.1 g of brown oil) was stirred first with MTB and then with MTB/n-pentane 1:1, and afforded 5.9 g of amorphous solid (MS (ESI) m/z 234.25 [M+H$^+$]).

B4) 5-Methoxy-1-methyl-3-piperidin-4-yl-1H-indole

Preparation took place as described in WO 02/50067 (page 56).

B5) 4-(5-Methyl-1-benzofuran-3-yl)piperidine

Preparation took place by reacting 4-chloroanisole with 1-acetylpiperidine-4-carbonyl chloride to give the intermediate (1-acetylpiperidin-4-yl)-(5-chloro-2-hydroxyphenyl)methanone in analogy to Strupczewski et al., J. Med. Chem. 1985, 28, 761-69. Alkylation of the OH function with methyl bromoacetate was followed by cyclization in analogy to Kaltenbronn et al, Eur. J. Med. Chem. 1997, 32 (5), 425-431, to give methyl 3-(1-acetylpiperidin-4-yl)-5-methyl-1-benzofuran-2-carboxylate. Hydrolysis of the ester function, decarboxylation and subsequent hydrolysis of the acetyl group resulted in 4-(5-methyl-1-benzofuran-3-yl)piperidine (see also DE 2537837 for the preparation).

B6) 4-(5-Chloro-1-benzofuran-3-yl)piperidine

Preparation took place in analogy to the preparation of 4-(5-methyl-1-benzofuran-3-yl)piperidine (see B5).

B7) 3-Piperidin-4-yl-1H-indole

Is commercially available.

B8) 3-Piperidin-4-yl-1H-pyrrolo[2,3-b]pyridine

Preparation took place by hydrogenation of 3-(1,2,3,6-tetrahydropyridin-4-yl)-1H-pyrrolo[2,3-b]pyridine with palladium on carbon in ethanol with the addition of hydrochloric acid.

B9) 3-(1,2,3,6-Tetrahydropyridin-4-yl)-1H-indole

Preparation took place as described in DE 2738646 (page 15).

B10) 3-(1,2,3,6-Tetrahydropyridin-4-yl)-1H-pyrrolo[2,3-b]pyridine

Preparation took place as described in WO 00/64898 (page 7).

B11) 4-[5-(4-Chlorophenyl)-1H-pyrazol-3-yl]piperidine

Is commercially available.

B12) 4-[5-(2-Thienyl)-1H-pyrazol-3-yl]piperidine

Is commercially available.

B13) 1-Piperidin-4-yl-1H-1,2,3-benzotriazole

Is commercially available.

B14) 1-Piperidin-4-yl-1H-benzimidazole

Is commercially available.

B15) 1-(1-Phenyl-1H-tetrazol-5-yl)piperazine

Preparation took place by reacting 5-chloro-1-phenyl-1H-tetrazole with tert-butyl piperazine-1-carboxylate in DMF at 40° C.

C Preparation of the Final Products of the Formula (I)

Unless indicated otherwise, the following compounds were prepared by reacting suitable starting materials of the formula (VI) with suitable starting materials of the formula (VII) as explained in detail in Example 9:

EXAMPLE 1

4-(5-methyl-1,2-benzisoxazol-3-yl)-1-[2-(4-oxo-5,8-dihydro-4H-pyrano[4',3':4,5]thieno[2,3-d]pyrimidin-3(6H)-yl)ethyl]piperazin-1-ium fumarate ESI-MS [M+H$^+$]=452.
$^{13}$C-NMR (100.6 MHz, DMSO-d$_6$) δ: 20.5, 26.0, 42.3, 47.7 (2 C), 51.9 (2 C), 55.8, 63.8, 64.2, 109.5, 115.6, 121.3, 122.0, 128.4, 130.4, 131.2, 131.9, 148.2, 156.9, 160.6, 161.7, 162.2 ppm. (plus two fumarate signals).

EXAMPLE 2

3-{2-[4-(5-methyl-1,2-benzisoxazol-3-yl)piperazin-1-yl]ethyl}-3,5,6,8-tetrahydro-4H-thiopyrano[4',3':4,5]thieno[2,3-d]pyrimidin-4-one

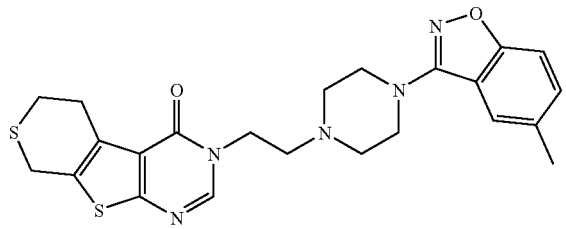

ESI-MS [M+H$^+$]=468.
$^{13}$C-NMR (100.6 MHz, DMSO-d$_6$) δ: 20.3, 24.5, 24.6, 27.2, 45.0 (2 C), 50.7 (3 C), 54.3, 109.4, 115.1, 121.6, 121.8, 129.2, 130.4, 131.3, 131.9, 147.7, 157.0, 159.5, 160.8, 161.8 ppm.

EXAMPLE 3

3-{(1S)-1-methyl-2-[4-(5-methyl-1,2-benzisoxazol-3-yl)piperazin-1-yl]ethyl}-3,5,6,8,-tetrahydro-4H-pyrano[4',3':4,5]thieno[2,3-d]pyrimidin4-one

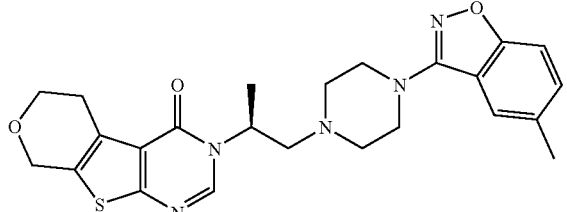

ESI-MS [M+H$^+$]=466.
$^{13}$C-NMR (100.6 MHz, DMSO-d$_6$) δ: 18.1, 20.4, 26.0 (2C), 47.6 (2C), 52.0 (2C), 60.9, 63.8, 64.2, 109.5, 115.5, 120.9, 122.0, 128.6, 130.4, 131.1, 131.8, 145.8, 156.9, 160.4, 161.6, 161.7 ppm.

EXAMPLE 4

3-{2-[4-(1,2-Benzisothiazol-3-yl)piperazin-1-yl]ethyl}-7-methyl-5,6,7,8-tetrahydropyrido[4',3':4,5]thieno[2,3-d]pyrimidin-4(3H)-one

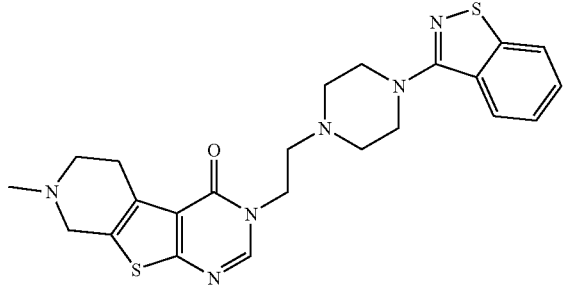

Melting point: 82-84° C.; ESI-MS [M+H$^+$]=467.

EXAMPLE 5

3-{2-[4-(4-Chloro-1,2-benzisothiazol-3-yl)piperazin-1-yl]ethyl}-7-methyl-5,6,7,8-tetrahydropyrido[4',3':4,5]thieno[2,3-d]pyrimidin-4(3H)-one

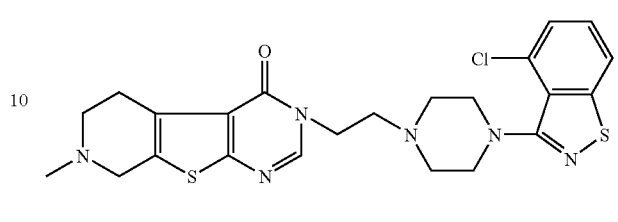

Melting point: 88-89° C.; ESI-MS [M+H$^+$]=501.

EXAMPLE 6

7-Methyl-3-(2-{4-[5-(trifluoromethyl)-1,3-benzothiazol-2-yl]piperazin-1-yl}ethyl)-5,6,7,8-tetrahydropyrido[4',3':4,5]thieno[2,3-d]pyrimidin-4(3H)-one

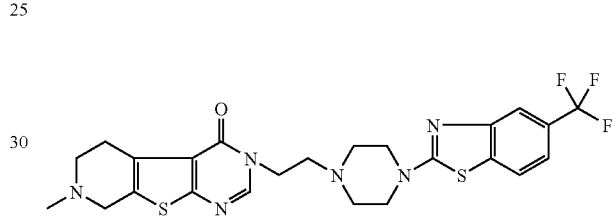

Melting point: 166-67° C.; ESI-MS [M+H$^+$]=535.

EXAMPLE 7

3-{2-[4-(6-Chloro-1,3-benzothiazol-2-yl)piperazin-1-yl]ethyl}-7-methyl-5,6,7,8-tetrahydropyrido[4',3':4,5]thieno[2,3-]pyrimidin-4(3H)-one

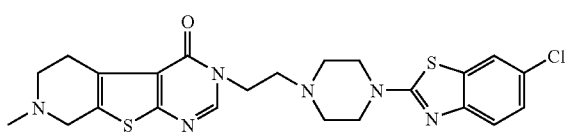

Melting point: 160-162° C.; ESI-MS [M+H$^+$]=501.

EXAMPLE 8

3-{2-[4-(1H-Benzimidazol-2-yl)piperazin-1-yl]ethyl}-7-methyl-5,6,7,8-tetrahydropyrido[4',3':4,5]thieno[2,3-d]pyrimidin-4(3H)-one

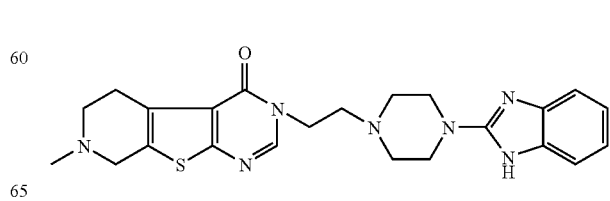

Melting point: 227-229° C.; ESI-MS [M+H$^+$]=450.

EXAMPLE 9

7-Methyl-3-{2-[4-(5-methyl-1,2-benzisoxazol-3-yl)piperazin-1-ium-1-yl]ethyl}-4-oxo-3,4,5,6,7,8-hexahydropyrido[4',3':4,5]thieno[2,3-d]spyrimidin-7-ium dichloride

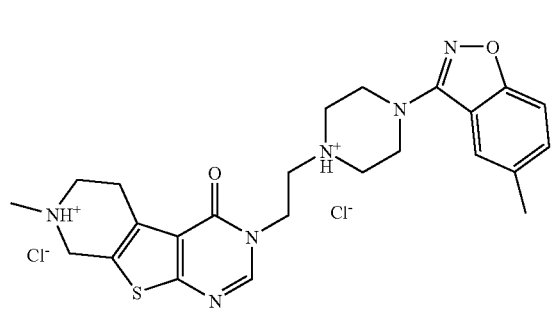

3-(2-Chloroethyl)-7-methyl-5,6,7,8-tetrahydropyrido[4',3':4,5]thieno[2,3-d]pyrimidin-4(3H)-one (2.5 g, 8.81 mol; preparation: Example A3) was stirred together with 3-piperazin-1-yl-5-methyl-1,2-benzisoxazole (2.49 g, 11.45 mmol), diisopropylethylamine (15.4 ml, 88.1 mmol), sodium bromide (4.53 g, 44.05 mmol) and N-methyl-2-pyrrolidone (40 ml) at 70° C. for 4 days. After cooling, N-methyl-2-pyrrolidone and excess diisopropylethylamine were removed under high vacuum, the residue was added to water, the aqueous phase was extracted several times with ethyl acetate, and the organic phases were washed with water, dried over magnesium sulfate and concentrated in vacuo. The very impure crude product was chromatographed on silica gel (eluent: methylene chloride with slowly increasing methanol content (0-50%)). This resulted in 0.9 g of 7-methyl-3-{2-[4-(5-methyl-1,2-benzisoxazol-3-yl)piperazin-1-yl]ethyl}-5,6,7,8-tetrahydropyrido[4',3':4,5]thieno-[2,3-d]pyrimidin-4(3H)-one (yield: 22%) being obtained as a solid product which was converted into the corresponding dihydrochloride with ethereal hydrochloric acid.

$^{13}$C-NMR (125.69 MHz, DMSO-$d_6$) δ: 163.1, 161.8, 159.7, 157.3, 148.6, 132.3, 131.7, 127.8, 124.3, 121.7, 120.6, 115.1, 109.7, 54.0, 50.6(2C), 50.4, 49.6, 44.7 (2C), 41.8, 40.1, 22.7, 20.5 ppm.

ESI-MS [M+H+]=465.

EXAMPLE 10

3-{2-[4-(1,3-Benzoxazol-2-yl)piperazin-1-yl]ethyl}-7-methyl-5,6,7,8-tetrahydropyrido[4',3':4,5]thieno[2,3-d]pyrimidin-4(3H)-one

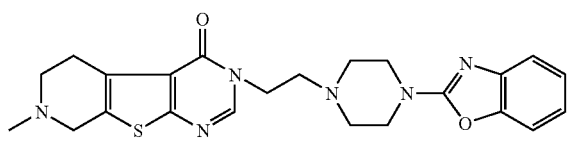

Melting point: 130-132° C.; ESI-MS [M+H+]=451.

EXAMPLE 11

3-{2-[4-(1,3-Benzothiazol-2-yl)piperazin-1-yl]ethyl}-7-methyl-5,6,7,8-tetrahydropyrido[4',3':4,5]thieno[2,3-d]pyrimidin-4(3H)-one

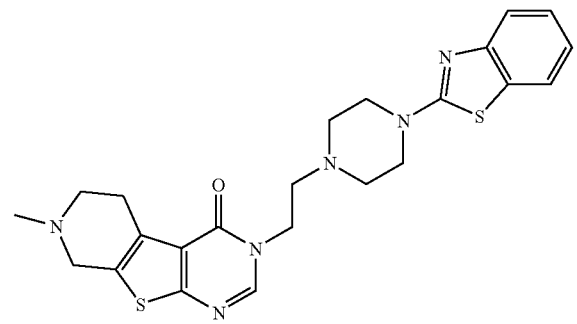

Melting point: 151-153° C.; ESI-MS [M+H+]=467.

EXAMPLE 12

3-{2-[4-(1,2-Benzisoxazol-3-yl)piperazin-1-ium-1-yl]ethyl}-7-methyl-4-oxo-3,4,5,6,7,8-hexahydropyrido[4',3':4,5]thieno[2,3-d]pyrimidin-7-ium dichloride

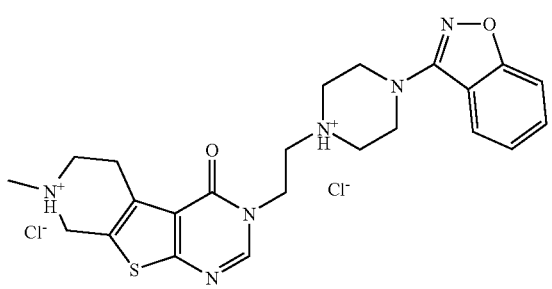

ESI-MS [M+H+]=451.

$^1$H-NMR (500 MHz, DMSO-$d_6$) δ: 8.52 (m, 1H), 8.04 (m, 1H), 7.63 (m, 2H), 7.34 (m, 1H), 4.62 (m, 1 H), 4.45 (m, 3H), 4.20 (m, 2H), 3.80-3.20 (m, 12H, overlapped by water) 2.95 (s, 3H).

EXAMPLE 13

3-{2-[4-(1H-Indazol-3-yl)piperazin-1-yl]ethyl}-7-methyl-5,6,7,8-tetrahydropyrido[4',3':4,5]thieno[2,3-d]pyrimidin-4(3H)-one

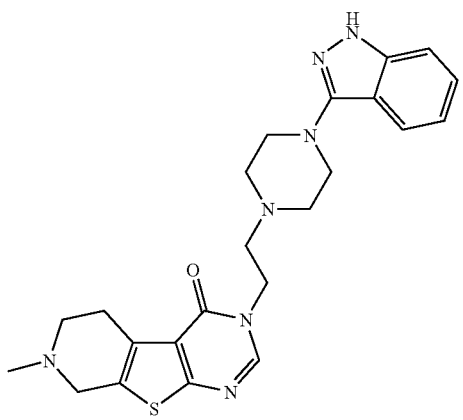

ESI-MS [M+H⁺]=450.
¹H-NMR (500 MHz, DMSO-d₆) δ: 11.96 (s, 1H), 8.31 (s, 1H), 7.72 (d, 1H), 7.33 (d, 1H), 7.27 (m, 1H), 6.96 (m, 1H), 4.11 (m, 2H), 3.56 (s, 2H), 3.35-3.25 (m, 4H, overlapped by water), 2.96 (m, 2H), 2.68-2.60 (m, 8H), 2.37 (s, 3H).

EXAMPLE 14

4-(7-Methyl-1,2-benzisoxazol-3-yl)-1-[2-(7-methyl-4-oxo-5,6,7,8-tetrahydropyrido[4',3':4,5]thieno[2,3-d]pyrimidin-3(4H-yl)ethyl]piperazin-1-ium chloride

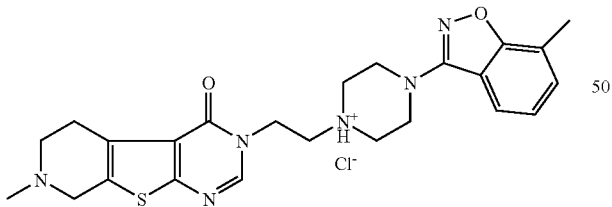

The title compound was obtained by reacting 3-piperazin-1-yl-7-methyl-1,2-benzisoxazole with 3-(2-chloroethyl)-7-methyl-5,6,7,8-tetrahydropyrido[4',3':4,5]thieno[2,3-d]pyrimidin-4-one and subsequent purification by chromatography on silica gel, and then converted into the corresponding fumarate. (CH2Cl2/CH3OH 0-8%); 70 mg; MS (ES I) m/z 465 [M+H⁺].
¹H-NMR (500 MHz, DMSO-d₆) δ: 8.35 (s, 1H), 7.78 (d, 1H), 7.47 (d, 1H), 7.19 (m, 1H), 6.61 (s, 2H), 4.12 (m, 2H), 3.65 (s, 2H), 3.44 (m, 4H), 2.98 (m, 2H), 2.77 (m, 2H), 2.68 (m, 6H), 2.45 (s, 3H), 2.42 (s, 3H).

EXAMPLE 15

4-(5-Methoxy-1,2-benzisoxazol-3-yl)-1-[2-(7-methyl-4-oxo-5,6,7,8-tetrahydropyrido[4',3':4,5]thieno[2,3-d]pyrimidin-3(4H)-yl)ethyl]piperazin-1-ium chloride

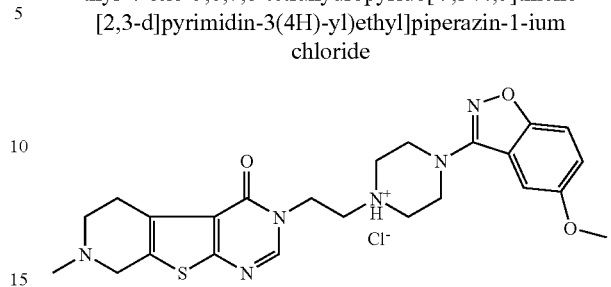

¹³C-NMR (125.76 MHz, D₂O) δ: 163.8, 160.4, 159.2, 159.0, 155.3, 148.3, 127.8, 125.1, 121.4, 120.8, 114.9, 111.3, 103.2, 56.5, 55.4, 52.0 (2C), 51.9, 51.2, 45.5 (2C), 42.6, 41.5, 22.9 ppm.
ESI-MS [M+H⁺]=481.

EXAMPLE 16

4-(5-Methoxy-1-methyl-1H-indol-3-yl)-1-[2-(7-methyl-4-oxo-5,6,7,8-tetrahydropyrido[4',3':4,5]thieno[2,3-d]pyrimidin-3(4H)-yl)ethyl]piperidinium chloride

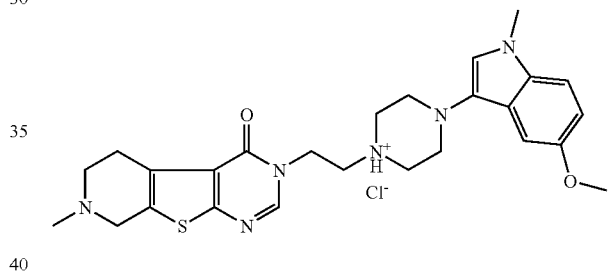

ESI-MS [M+H⁺]=492.

EXAMPLE 17

4-(5-Methyl-1-benzofuran-3-yl)-1-[2-(7-methyl-4-oxo-5,6,7,8-tetrahydropyrido[4',3':4,5]thieno[2,3-d]pyrimidin-3(4H)-yl)ethyl]piperidinium chloride

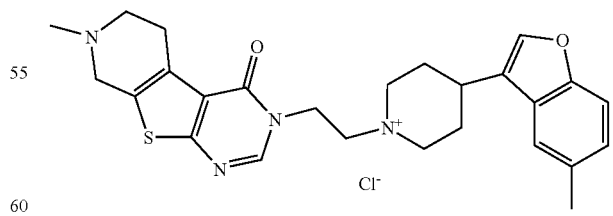

¹³C-NMR (125.76 MHz, D₂O) δ: 163.6, 159.0, 153.3, 148.0, 141.0, 132.6, 127.5, 126.4, 125.8, 124.7, 122.4, 121.1, 119.4, 111.1, 55.0, 53.5 (2C), 51.5, 50.8, 42.1, 41.4, 29.3, 28.8 (2C), 22.5, 20.3 ppm.
ESI-MS [M+H⁺]=483.

EXAMPLE 18

4-(5-Chloro-1-benzofuran-3-yl)-1-[2-(7-methyl-4-oxo-5,6,7,8-tetrahydropyrido[4',3':4,5]thieno[2,3-d]pyrimidin-3(4H)-yl)ethyl]piperidinium chloride

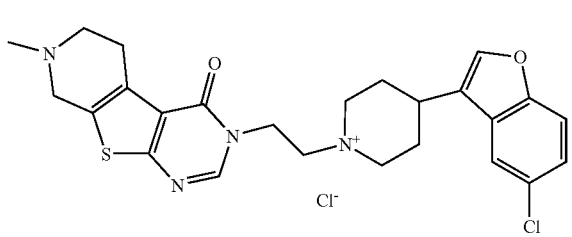

$^{13}$C-NMR (125.76 MHz, D$_2$O) δ: 163.6, 159.0, 1531.4, 148.0, 142.3, 127.7, 127.5, 127.4, 124.7, 124.5, 122.4, 121.0, 119.2, 112.6, 55.0, 53.4 (2C), 51.5, 50.8, 42.2, 41.4, 29.2, 28.8 (2C), 22.5 ppm.

ESI-MS [M+H$^+$]=483.

EXAMPLE 19

4-(1H-Indol-3-yl)-1-[2-(7-methyl-4-oxo-5,6,7,8-tetrahydropyrido[4',3':4,5]thieno[2,3-d]pyrimidin-3(4H)-yl)ethyl]piperidinium chloride

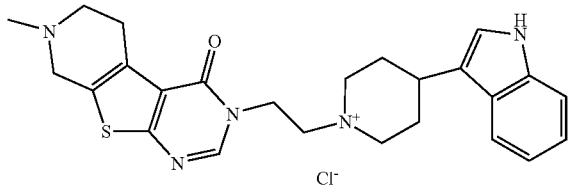

$^{13}$C-NMR (100.61 MHz, D$_2$O) δ: 163.6, 158.9, 147.9, 136.2, 127.4, 125.4, 125.0, 124.7, 122.0, 121.1, 119.1, 118.5, 117.4, 111.8, 54.9, 53.7 (2C), 51.5, 50.8, 42.2, 41.4, 30.4, 29.8 (2C), 22.5 ppm.

ESI-MS [M+H$^+$]=448.

EXAMPLE 20

3-{2-[4-(1H-Indol-3-yl)-3,6-dihydropyridin-1(2H)-yl]ethyl}-7-methyl-5,6,7,8-tetrahydropyrido[4',3':4,5]thieno[2,3-d]pyrimidin-4(3H)-one

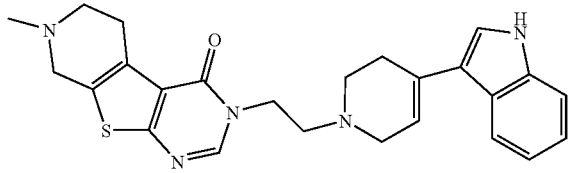

$^{13}$C-NMR (100.61 MHz, DMSO-d$_6$) δ: 161.9, 156.9, 148.0, 136.9, 130.3, 129.7, 128.9, 124.6, 122.7, 121.3, 121.1, 120.0, 119.1, 117.4, 115.8, 111.7, 55.7, 52.9 (2C), 51.2, 48.5, 44.9, 42.6, 28.4, 25.7 ppm.

ESI-MS [M+H$^+$]=446.

EXAMPLE 21

1-[2-(7-Methyl-4-oxo-5,6,7,8-tetrahydropyrido[4',3':4,5]thieno[2,3-d]pyrimidin-3(4H)-yl)ethyl]-4-(1H-pyrrolo[2,3-b]pyridin-3-yl)-1,2,3,6-tetrahydropyridinium acetate

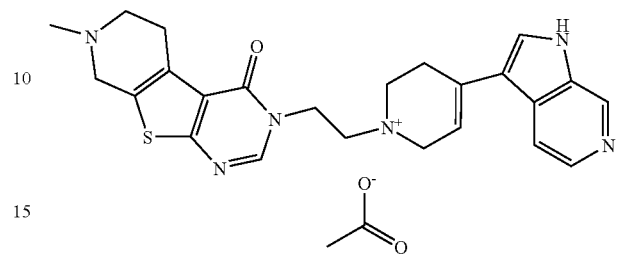

$^{13}$C-NMR (125.7 MHz, DMSO-d$_6$) δ: 162.9, 157.4, 149.0, 148.6, 142.9, 129.3, 128.1, 127.8, 124.5, 124.3, 120.7, 116.5, 115.9, 112.8 (2C), 53.7, 50.6, 50.5, 49.7, 48.6, 41.9, 40.5, 24.5, 22.9 ppm

ESI-MS [M+H$^+$]=447.

EXAMPLE 22

1-[2-(7-Methyl-4-oxo-5,6,7,8-tetrahydropyrido[4',3':4,5]thieno[2,3-d]pyrimidin-3(4H)-yl)ethyl]-4-(1H-pyrrolo[2,3-b]pyridin-3-yl)piperidinium acetate

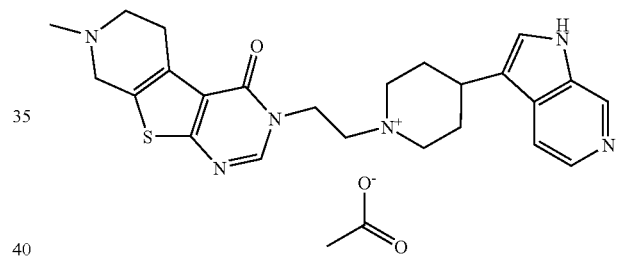

$^{13}$C-NMR (125.7 MHz, D$_2$O) δ: 164.0, 159.5, 148.4, 147.2, 142.1, 129.4, 127.9, 125.2, 122.2, 121.6, 119.6, 117.0, 115.7, 55.1, 53.7 (2C), 51.9, 51.2, 42.6, 41.9, 30.6, 29.7, 29.6, 23.0 ppm.

ESI-MS [M+H$^+$]=447.

EXAMPLE 23

4-[5-(4-Chlorophenyl)-1H-pyrazol-3-yl]-1-[2-(7-methyl-4-oxo-5,6,7,8-tetrahydropyrido[4',3':4,5]thieno[2,3-d]pyrimidin-3(4H)-yl)ethyl]piperidinium chloride

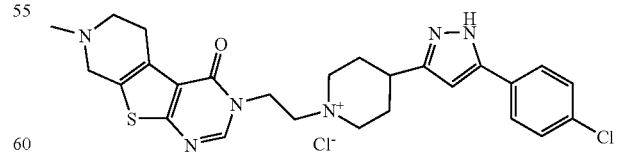

$^{13}$C-NMR (125,7 MHz, DMSO-d$_6$) δ: 161.2, 155.3, 148.2, 146.7, 144.1, 130.3, 128.7, 126.9 (2C), 126.1, 125.0 (2C), 122.6, 118.9, 97.6, 52.2, 49.9 (2C), 48.3, 47.6, 39.8, 38.5, 29.2, 26.4 (2C), 20.8 ppm

ESI-MS [M+H$^+$]=509.

EXAMPLE 24

1-[2-(7-Methyl-4-oxo-5,6,7,8-tetrahydropyrido[4',3': 4,5]thieno[2,3-d]pyrimidin-3(4H)-yl)ethyl]-4-[5-(2-thienyl)-1H-pyrazol-3-yl]piperidinium chloride

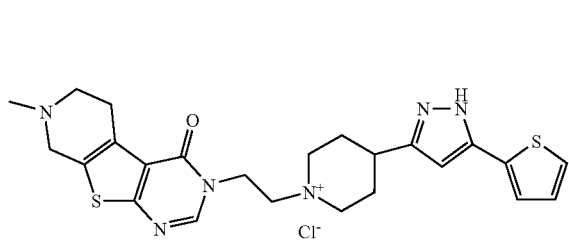

$^{13}$C-NMR (125.7 MHz, D$_2$O) δ: 166.7, 162.2, 153.1, 151.1, 146.5, 134.0, 131.3 (2C), 130.6, 129.6, 127.8, 124.3, 103.9, 58.1, 55.9, 54.5 (2C), 53.9, 45.2, 44.4, 33.7, 31.5 (2C), 25.6 ppm.
ESI-MS [M+H$^+$]=481.

EXAMPLE 25

3-{2-[4-(1H-1,2,3-Benzotriazol-1-yl)piperidinium-1-yl]ethyl}-7-methyl-4-oxo-3,4,5,6,7,8-hexahydropyrido[4',3':4,5]thieno[2,3-d]pyrimidin-7-ium dichloride

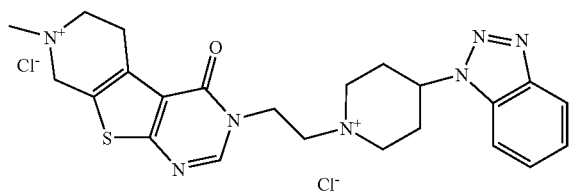

$^{13}$C-NMR (125.7 MHz, D$_2$O) δ:163.9, 159.4, 148.4, 144.9, 132.7, 128.6, 127.9, 125.7, 122.2, 125.2, 121.5, 119.0, 110.6, 55.2, 53.1, 52.1, 51.9(2C), 51.2, 42.6, 42.0, 28.9,. 22.9 ppm.
ESI-MS [M+H$^+$]=450.

EXAMPLE 26

4-(1H-Benzimidazol-1-yl)-1-[2-(7-methyl-4-oxo-5,6,7,8-tetrahydropyrido[4',3':4,5]thieno[2,3-d]pyrimidin-3(4H)-yl)ethyl]piperidinium chloride

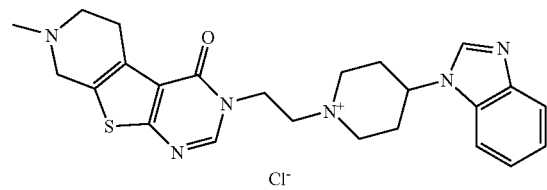

ESI-MS [M+H$^+$]449.

Example 27

1-[2-(7-Methyl-4-oxo-5,6,7,8-tetrahydropyrido[4',3': 4,5]thieno[2,3-d]pyrimidin-3(4H)-yl)ethyl]-4-(1-phenyl-1H-tetrazol-5-yl)piperazin-1-ium chloride

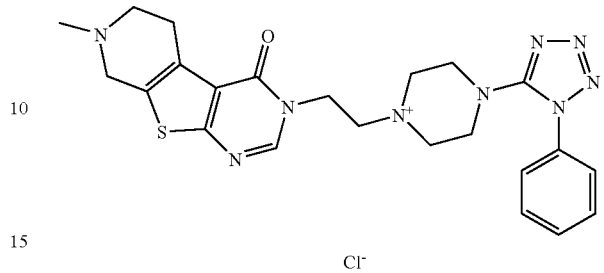

ESI-MS [M+H$^+$]=478.

EXAMPLE 28

3-{2-[4-(1-Benzothien-3-yl)-3,6-dihydropyridin-1 (2H)-yl]ethyl}-7-methyl-5,6,7,8-tetrahydropyrido[4', 3':4,5]thieno[2,3-d]pyrimidin-4(3H)-one

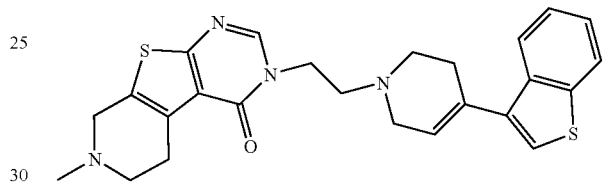

EXAMPLE 29

7-Methyl-3-{2-[4-(3-phenyl-1,2,4-thiadiazol-5-yl) piperazin-1-yl]ethyl}-5,6,7,8-tetrahydropyrido[4',3': 4,5]thieno[2,3-d]pyrimidin-4(3H)-one

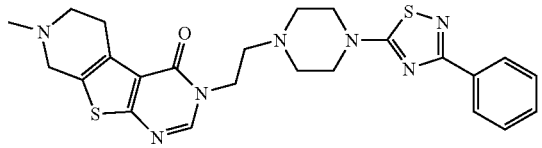

EXAMPLE 30

7-Methyl-3-{2-[4-(4-phenyl-1,3-thiazol-2-yl)piperazin-1-yl]ethyl}-5,6,7,8-tetrahydropyrido[4',3':4,5] thieno[2,3-d]pyrimidin-4(3H)-one

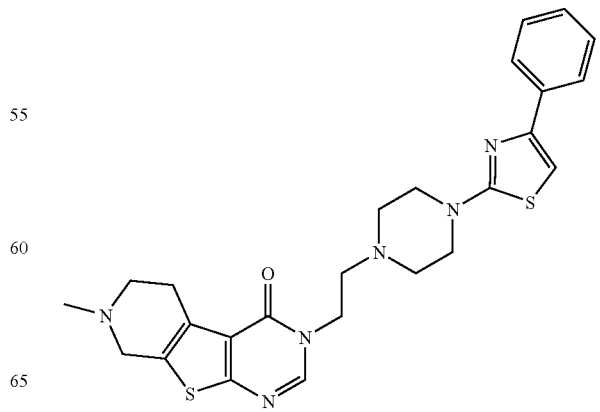

EXAMPLE 31

4-(2,1-Benzisothiazol-3-yl)-1-[2-(7-methyl-4-oxo-5,6,7,8-tetrahydropyrido[4',3':4,5]thieno[2,3-d]pyrimidin-3(4H)-yl)ethyl]piperazin-1-ium chloride

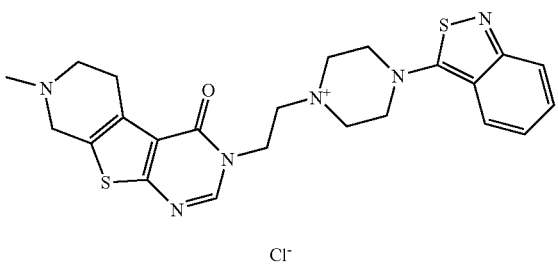

Cl⁻

EXAMPLE 32

3-{2-[4-(5-methoxy-1H-indol-3-yl)-3,6-dihydropyridin-1(2H)-yl]ethyl}-7-methyl-5,6,7,8,-tetrahydropyrido[4',3':4,5]thieno[2,3-d]pyrimidin-4(3H)-one

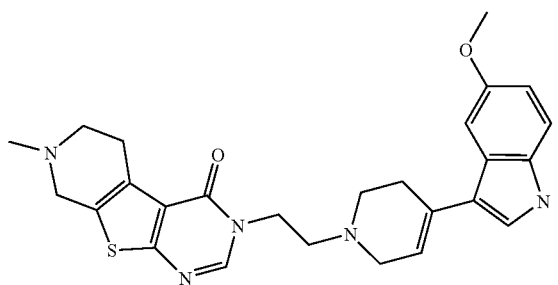

EXAMPLE 33

4-(5-Methoxy-1-methyl-1H-indol-3-yl)-1-[2-(7-methyl-4-oxo-5,6,7,8-tetrahydropyrido[4',3':4,5]thieno[2,3-d]pyrimidin-3(4H)-yl)ethyl]-1,2,3,6-tetrahydropyrimidinium chloride

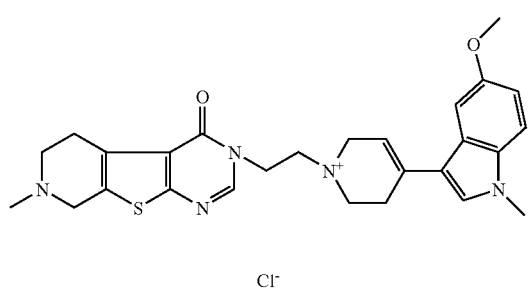

Cl⁻

EXAMPLE 34

3-{(1R)-1-methyl-2-[4-(5-methyl-1,2-benzisoxazol-3-yl)piperazin-1-yl]ethyl}-tetrahydro-4H-pyrano[4',3':4,5]thieno[2,3-d]pyrimidin-4-one

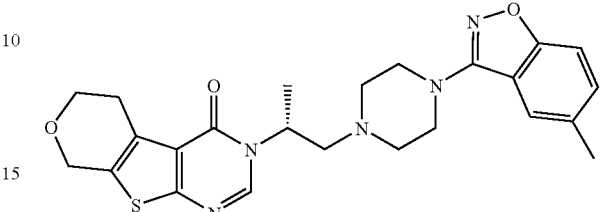

ESI-MS [M+H⁺]=466.

Receptor Binding Studies

Membrane Preparation

HEK293 cells which expressed $5\text{-}HT_{1A}$ or $5\text{-}HT_{1B}$ receptors were cultivated in RPMI 1640 (Life Technologies, Eggenstein, Germany) comprising 10% fetal calf serum. All the culture media were supplemented with 2 mM L-glutamine and 400 mg/l Geneticin G418 (Life Technologies). The cells were grown in a moist atmosphere with 6% $CO_2$ at 37° C. and detached with a buffer comprising 0.0004% EDTA, 0.02% EGTA, 2.68 mM KCl, 1.47 mM $KH_2PO_4$, 6.46 mM $Na_2HPO_4$ and 136.9 mM NaCl (pH 7.4). The harvested cells were washed once with cold phosphate-buffered Dulbecco's saline solution (PBS), centrifuged (200×g; 10 minutes) and adjusted to a cell density of $10^8$ cells per cryovial. After renewed centrifugation, the pellets were resuspended in 1 ml of ice-cold dissolving buffer (5 mM Tris/HCl (pH 7.4), 10% glycerol) and incubated at 4° C. for 30 minutes. The suspension was then centrifuged at 900×g for 10 minutes, the supernatants were removed, and the pellets were stored in liquid nitrogen until used.

Binding Experiments

Initially, the affinities of the radio ligands ((³H)-8-OH-DPAT for $5\text{-}HT_{1A}$ receptors; or (³H)-5-CT for $5\text{-}HT_{1B}$ receptors) were calculated from saturation plots where triplicate determinations of the specific and nonspecific binding were carried out for each test concentration. Each sample was composed of 50 µg of cellular proteins of the particular membrane preparation, the radio ligand with or without competing compound (5-HT) in a total volume of 0.5 ml. A buffer consisting of 50 mM Tris/HCl (pH 7.4) and 5 mM $CaCl_2$ was used. Incubation was at 22° C. for 9 minutes.

For Ki determinations, the test compounds were titrated three times in displacement experiments against a fixed concentration of radio ligand ((0.2 nM (³H)-8-OH-DPAT; or 0.2 nM (³H)-5-CT). The other test conditions corresponded to those described for the saturation experiments. The total and the nonspecific binding (10 µM 5-HT as competitor of $5\text{-}HT_{1A}$ and 100 µM for $5\text{-}HT_{1B}$) was determined for each experimental series.

The incubation for binding and displacement was terminated by filtering and washing the samples on glass fiber filters (GF/B) using a Skatron 7200 cell harvester (Zinsser, Frankfurt, Germany). The sample filters were transferred into scintillation vials comprising 5 ml of scintillator (Ultima Gold XR) and agitated for 1 hour, and then measured in a liquid scintillation counter. Saturation and competition plots were calculated with the aid of a computer program based on LIGAND (Mundson, P J and Reodbard, D; Anal. Biochem. 107, 220 (1980)).

The following binding affinities were determined:

| Example | Ki 5HT$_{1A}$ [nM] | Ki 5HT$_{1B}$ [nM] |
|---|---|---|
| 4 | 1.4 | 0.9 |
| 9 | 6.2 | 4.5 |
| 13 | 11.5 | 3.5 |
| 15 | 13.7 | 7.9 |
| 16 | 1.3 | 2.3 |
| 20 | 1.2 | 1.0 |
| 21 | 14.6 | 1.0 |
| 22 | 17.0 | 2.7 |
| 24 | 98.3 | 286.1 |
| 28 | 1.3 | 2.0 |
| 31 | 42.7 | 24.3 |
| 32 | 0.5 | 0.6 |

We claim:

1. A compound of the formula (I)

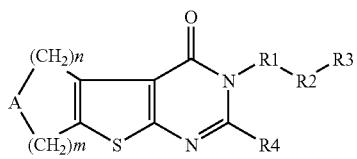

in which
A is O, S, SO, NR5 or CH$_2$;
R5 is H, C$_{1-5}$-alkyl, aryl, aralkyl, acyl or alkoxycarbonyl;
R4 is H or methyl;
n is 1 or 2;
m is 1 or 2;
R1 is C$_{1-8}$-alkylene;
R2 is a group of the formula

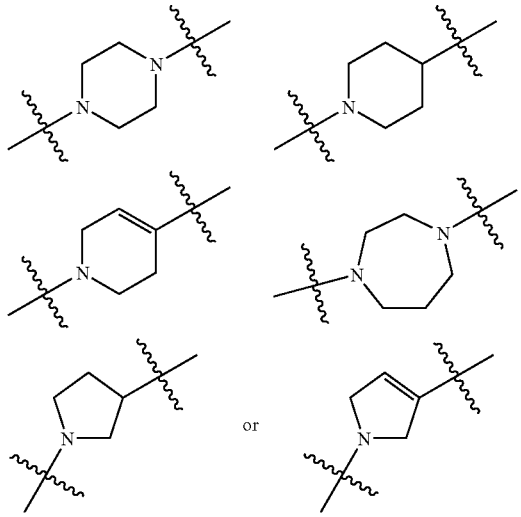

or

R3 is 5-membered heteroaryl which may be fused to an aryl or heteroaryl radical, where the heteroaryl and, optionally, the fused aryl or heteroaryl radical may have 1, 2 or 3 substituents selected independently of one another from C$_{1-5}$-alkyl, C$_{1-5}$-alkoxy, C$_{1-5}$-alkylthio, halogen, CN, halo-C$_{1-5}$-alkyl, halo-C$_{1-5}$-alkoxy, hydroxy, —NH$_2$, —N(R6)$_2$, —NH(R6), aryl, aryloxy, aralkyl, aralkyloxy and heteroaryl, where the substituents aryl, aryloxy, aralkyl, aralkyloxy and heteroaryl may have 1, 2 or 3 substituents selected independently of one another from C$_{1-5}$-alkyl, C$_{1-5}$-alkoxy, C$_{1-5}$-alkylthio, halogen, CN, halo-C$_{1-5}$-alkyl, halo-C$_{1-5}$-alkoxy, hydroxy, —NH$_2$, —N(R6)$_2$ and —NH(R6); and the radicals R6 are independently of one another C$_{1-5}$-alkyl, and physiologically tolerated salts thereof.

2. The compound according to claim 1, wherein R3 is 1H-indol-3-yl, 1H-pyrrolo[2,3-b]pyridin-3-yl, 1-benzofuran-3-yl, 1-benzothien-3-yl, 1H-indazol-3-yl, 1H-benzimidazol-1-yl, 1H-benzimidazol-2-yl, 1H-benzotriazol-1-yl, 1,3-benzoxazol-2-yl, 1,2-benzisoxazol-3-yl, 1,3-benzothiazol-2-yl, 1,2-benzisothiazol-3-yl, pyrazol-3-yl, 1H-tetrazol-5-yl, 1,3-thiazol-2-yl or 1,2,4-thiadiazol-5-yl, which may have 1, 2 or 3 substituents selected independently of one another from C$_{1-5}$-alkyl, C$_{1-5}$-alkoxy, halogen, CN, SCH$_3$, trifluoromethyl, hydroxy, —N(C$_{1-5}$-alkyl)$_2$, —NH(C$_{1-5}$-alkyl), —NH$_2$, aryl, aryloxy, aralkyl, aralkyloxy and heteroaryl, where the substituents aryl, aryloxy, aralkyl, aralkyloxy and heteroaryl may have 1, 2 or 3 substituents selected independently of one another from C$_{1-5}$-alkyl, C$_{1-5}$-alkoxy, halogen, CN, SCH$_3$, trifluoromethyl, hydroxy, —N(C$_{1-5}$-alkyl)$_2$, —NH(C$_{1-5}$-alkyl) or —NH$_2$.

3. The compound according to claim 2, wherein R3 is a radical of the formula

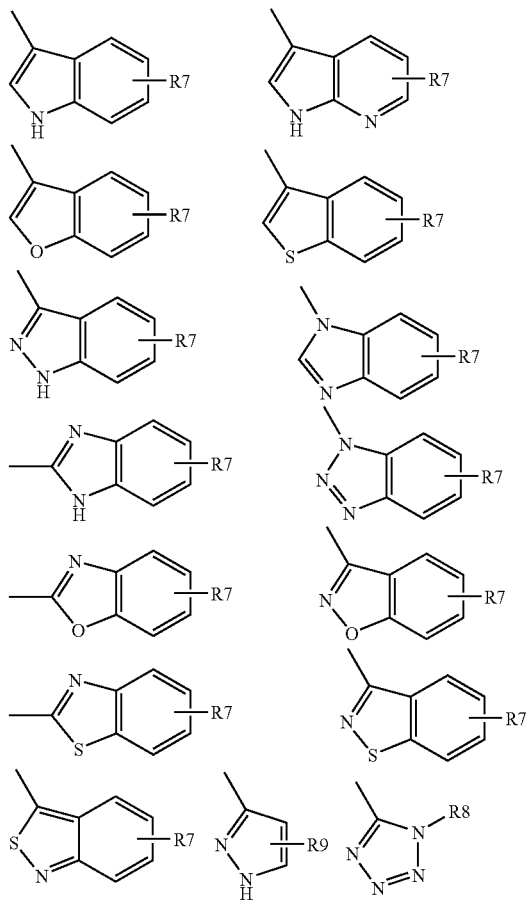

-continued

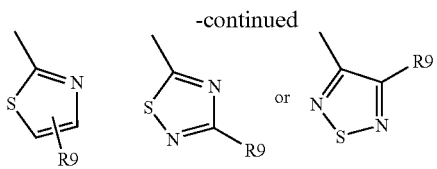

in which
R7 is H, $C_{1-5}$-alkyl, $C_{1-5}$-alkoxy, $C_{1-5}$-alkylthio, halogen, CN, halo-$C_{1-5}$-alkyl, halo-$C_{1-5}$-alkoxy, hydroxy, —$NH_2$, —$N(R6)_2$ or —NH(R6); and
R8 is H, $C_{1-5}$-alkyl, aryl, aralkyl or heteroaryl;
R9 is H, $C_{1-5}$-alkyl, $C_{1-5}$-alkoxy, $C_{1-5}$-alkylthio, halogen, CN, halo-$C_{1-5}$-alkyl, halo-$C_{1-5}$-alkoxy, hydroxy, —$NH_2$, —$N(R6)_2$, —NH(R6), aryl, aryloxy, aralkyl, aralkyloxy or heteroaryl, where aryl, aryloxy, aralkyl, aralkyloxy or heteroaryl may have 1, 2 or 3 substituents selected independently of one another from $C_{1-5}$-alkyl, $C_{1-5}$-alkoxy, $C_{1-5}$-alkylthio, halogen, CN, halo-$C_{1-5}$-alkyl, halo-$C_{1-5}$-alkoxy, hydroxy, —$NH_2$, —$N(R6)_2$ and —NH(R6); and the radicals
R6 have the meaning indicated in claim 1.

4. The compound according to claim 3, wherein R3 is a radical of the formula

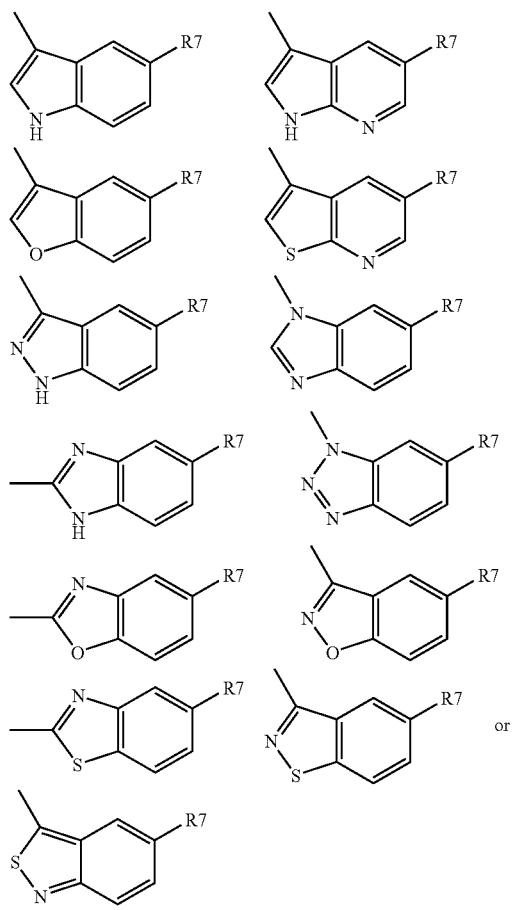

in which R7 is as defined in claim 3.

5. The compound according to claim 3, wherein R3 is a radical of the formula

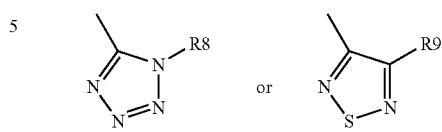

where R8 and R9 are as defined in claim 3.

6. The compound according to claim 4, wherein R7 is H, $C_{1-5}$-alkyl, preferably methyl, halogen, preferably chlorine, or halo-$C_{1-5}$-alkyl.

7. The compound according to claim 5, wherein R8 is $C_{1-5}$-alkyl or aryl.

8. The compound according to claim 5, wherein R9 is $C_{1-5}$-alkoxy, aryl which may be substituted, or heteroaryl.

9. The compound according to claim 1, wherein A is O, S or NR5, where R5 is as defined in claim 1.

10. The compound according to claim 1, wherein R4 is hydrogen.

11. The compound according to claim 1, wherein n is 2 and m is 1 or n is 1 and m is 2.

12. The compound according to claim 1, wherein R1 is eth-1,2-ylene, prop-1,3-ylene, prop-1,2-ylene, 2-methyl-prop-1,3-ylene, but-1,2-ylene or but-1,3-ylene.

13. The compound according to claim 1, wherein R2 is a group of the formula

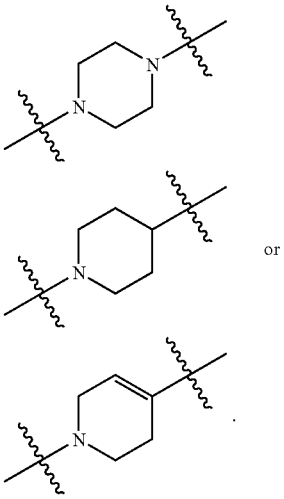

14. The compound according to claim 1, wherein
R4 is hydrogen;
n, m are 2, 1 or 1, 2;
R1 is eth-1,2-ylene, prop-1,3-ylene, prop-1,2-ylene, 2-methylprop-1,3-ylene, but-1,2-ylene or but-1,3-ylene;
R2 is a group of the formula

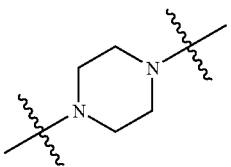

-continued

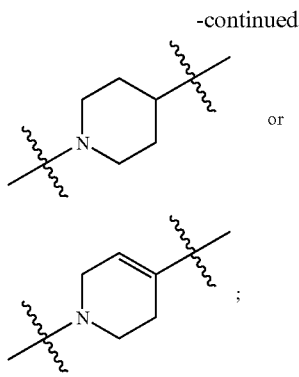

and

R3 is as defined in claim 1.

15. The compound according to claim 14, namely 3-substituted 5,6,7,8-tetrahydropyrido[4',3':4,5]thieno[2,3-d]pyrimidin-4(3H)-one derivatives;

3-substituted 3,5,6,8-tetrahydro-4H-pyrano[4',3':4,5]thieno[2,3-d]pyrimidin4-one derivatives, or 3-substituted 3,5,6,8-tetrahydro-4H-thiopyrano[4',3';4,5]thieno[2,3-d]pyrimidin-4-one derivatives.

16. A process for preparing a compound according to claim 1 a) by reacting a compound of the formula (II)

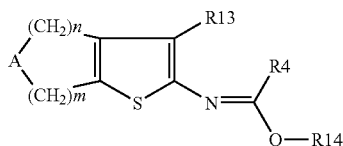

in which A, n, m and R4 have one of the meanings indicated in claim 1; R13 is CN or C,-3-alkyl-O—CO—, and R14 is C1.3-alkyl, with a primary amine of the formula (III)

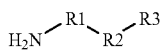

in which R1, R2 and R3 have one of the meanings indicated in claim 1, and isolating and, optionally, converting the resulting compound into a physiologically tolerated salt thereof, or b1) by reacting a compound of the formula (II)

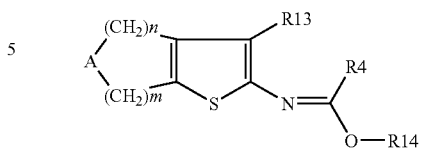

in which A, n, m and R4 have one of the meanings indicated in claim 1; R13 is CN or $C_{1-3}$-alkyl-O—CO—, and R14 is $C_{1-3}$-alkyl, with a primary amine of the formula (IV)

in which R1 has one of the meanings indicated in claim 1;

b2) reacting the resulting compound of the formula (V)

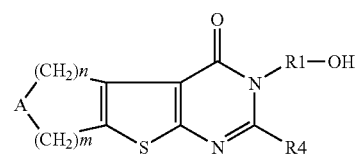

in which A, n, m, R4 and RI have one of the meanings indicated in claim 1, with a halogenating agent; and b3) reacting the resulting compound of the formula (VI)

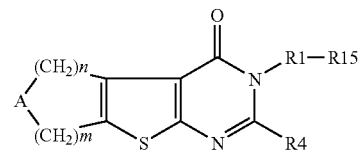

in which A, n, m, R4 and R1 have one of the meanings indicated in claim 1, and R15 is halogen, with a secondary amine of the formula (VII)

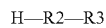

in which R2 and R3 have one of the meanings indicated in claim 1, and isolating and, optionally, converting the resulting compound into a physiologically tolerated salt thereof.

17. A pharmaceutical composition comprising at least one compound according to claim 1 and physiologically acceptable aids.

18. A method for treatment of depression which comprises administering an effective amount of a compound according to claim 1 to an individual in need thereof.

* * * * *